US007226597B2

(12) United States Patent
Ballard et al.

(10) Patent No.: US 7,226,597 B2
(45) Date of Patent: Jun. 5, 2007

(54) **MUTANTS OF *CLOSTRIDIUM DIFFICILE* TOXIN B AND METHODS OF USE**

(75) Inventors: Jimmy D. Ballard, Norman, OK (US); Lea M. Spyres, Smithville, TX (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 614 days.

(21) Appl. No.: 10/463,957

(22) Filed: Jun. 17, 2003

(65) Prior Publication Data

US 2004/0028705 A1 Feb. 12, 2004

Related U.S. Application Data

(60) Provisional application No. 60/389,685, filed on Jun. 17, 2002.

(51) Int. Cl.
*A61K 39/00* (2006.01)
*A61K 39/02* (2006.01)
*A61K 39/08* (2006.01)
*C07K 1/00* (2006.01)

(52) U.S. Cl. .................. 424/184.1; 424/190.1; 424/239.1; 530/350

(58) Field of Classification Search ............. 424/184.1, 424/190.1, 239.1; 530/350
See application file for complete search history.

(56) References Cited

FOREIGN PATENT DOCUMENTS

WO    PCT/US 03/19230    9/2004

OTHER PUBLICATIONS

Spyres et al. ,Infection and Immunity vol. 71, No. 6, pp. 3294-3301, 2003.*
Barroso et al. ,Microbial Pathogenesis vol. 16, pp. 297-303, 1994.*
Barroso et al. ,Nucleic Acid Research vol. 18, No. 13, p. 4004, 1990.*
Sequence alignment S10317.*
Busch, C., Hofmann, F., Gerhard, R., and Aktories; K. (2000) "Involvement of a conserved tryptophan residue in the UDP-glucose binding of large clostridial cytotoxin glycosyltransferases" *J Biol Chem* 275, 13228-13234.
Ciesla, W.P., Jr., and Bobak, D.A. (1998) "*Clostridium difficile* toxins A and B are cation-dependent UDP-glucose hydrolases with differing catalytic activities" *J Biol Chem* 273, 16021-16026.
Hofmann, F., Busch, C., and Aktories, K. (1998) "Chimeric clostridial cytotoxins: identification of the N-terminal region involved in protein substrate recognition" *Infect Immun* 66, 1076-1081.
Qa'Dan, M., Spyres, L.M., and Ballard, J.D. (2000) "pH-induced conformational changes in *Clostridium difficile* toxin B" *Infect Immun* 68, 2470-2474.
Qa'Dan, M., Spyres, L.M., and Ballard, J.D. (2001) "pH-Enhanced Cytopathic Effects of *Clostridium sordellii* Lethal Toxin" *Infect Immun* 69, 5487-5493.
Spyres, L.M., Qa'Dan, M., Meader, A., Tomasek, J.J., Howard, E.W., and Ballard, J.D. (2001) "Cytosolic delivery and characterization of the TcdB glucosylating domain by using a heterologous protein fusion" *Infect Immun* 69, 599-601.
Starnbach, M.N., and Bevan, M.J. (1994) "Cells infected with Yersinia present an epitope to class I MHC-restricted CTL" *Journal of Immunology* 153, 1603-1612.
Whilhite, D.C., and Blanke, S.R. (1998) Soluble Expression and One-Step Purification of Recombinant *Bacillus anthracis* Protective Antigen Protein and Peptide Letters 5, 273-278.
Barroso et al., "Mutagenesis of the *Clostridium difficile* toxin B gene and effect on cytotoxic activity", *Microbial Pathogenesis*, Academic Press Limited, New York, NY, US, vol. 16, No. 4, 1994, pp. 297-303, XP002100213.
Spyres et al., "Deletion Analysis of the *Clostridium difficile* Toxin B Glycosylation Domain", Abstracts of the General Meeting of the American Society for Microbiology, vol. 101, May 20, 2001, p. 94, XP002292782.
Spyres et al., "Mutational Analysis of the Enzymatic Domain of *Clostridium difficile* Toxin B Reveals Novel Inhibitors of the Wild-Type Toxin", *Infection and Immunity*, vol. 71, No. 6, Jun. 2003, pp. 3294-3301, XP002292785.

* cited by examiner

*Primary Examiner*—Jeffrey Siew
(74) *Attorney, Agent, or Firm*—Dunlap, Codding & Rogers, P.C.

(57) ABSTRACT

An active or passive vaccine utilizing purified non-toxic mutant TcdB toxins from *Clostridium difficile* for humans and animals against infections caused by *C. difficile* and/or *C. sordellii*. Persons most potentially affected by *C. difficile* infections include hospitalized patients, infants, and elderly persons. The TcdB toxin mutant of the vaccine preferably lacks the toxicity of a native *C. difficile* TcdB toxin. A serum comprising antibodies raised to the TcdB toxin mutant is also available for treating humans or animals against *C. difficile* infections. The serum may be used in a method for conferring passive immunity against *C. difficile*. Antibodies to the TcdB toxin mutant may be used in diagnostic tests or in treatments to clear TcdB toxin from bodily fluids. The mutant TcdB toxin may be produced by recombinant methods using cDNA encoding the toxin, the cDNA contained for example in a plasmid or host cell.

3 Claims, 8 Drawing Sheets

MUTANTS OF *CLOSTRIDIUM DIFFICILE* TOXIN B AND METHODS OF USE

CROSS REFERENCE TO RELATED APPLICATIONS

The present application claims benefit of U.S. Provisional 60/389,685, filed Jun. 17, 2002 which is explicitly incorporated herein by reference in its entirety.

STATEMENT REGARDING FEDERALLY SPONSORED RESEARCH OR DEVELOPMENT

Not Applicable.

BACKGROUND

Intracellular bacterial toxins enter cells, modify targets, and in many cases ultimately destroy the targeted cells thereby contributing to the disease process. Currently, there are no techniques for blocking intracellular virulence factors once they have entered the cytosol of cells. Further, no techniques exist which utilize inactive mutants derived from a toxin in order to inhibit the wild-type toxin at the intracellular cite.

*Clostridium difficile* is the leading cause of hospital acquired diarrhea and pseudomembranous colitis, a multifactorial disease involving steps in colonization, adherence, inflammation and cellular intoxication. TcdA and TcdB are two large clostridial toxins (LCTs) produced by *C. difficile* and are involved in development of pseudomembranous colitis. TcdB, (SEQ ID NO: 1), the focus of this study, glucosylates isoforms of small GTPases Rho, Rac and Cdc42 within the effector binding region at residues Threonine-37 (Rho) or Threonine-35 (Rac and Cdc42). The physiological impact of TcdB's activity includes disruption of tight junctions, increased epithelial permeability, as well as actin condensation and cell death.

TcdB can be divided into enzymatic, translocation and receptor binding domains, although detailed analysis of these regions has not been carried out to date. The first 546 amino acids of TcdB contain the enzymatic region, which is followed by a putative translocation and receptor-binding domain. Enzymatic activity appears to require the amino-terminal 546 residues since amino or carboxy terminal deletions of this fragment decrease activity. Within the enzymatic region, tryptophan 102 has been shown to be essential for UDP-glucose binding. A conserved DXD motif within LCTs is essential for LCT glucosyltransferase activity. Other studies, involving analysis of chimeras of the TcdB and TcsL enzymatic domain suggest residues 364 to 516 confer substrate specificity.

Steps in cell entry by TcdB have been broadly defined, yet events subsequent to entry are not well understood. For example, while we have a profile of the time-course for TcdB cell entry, very little is known about post-entry events that lead to glucosylation. Steps between membrane translocation and substrate interaction are not understood in TcdB intoxication. In fact almost no information exists in this regard for any intracellular toxin. In the cytosol, TcdB is capable of glucosylating multiple substrates, but whether inactivation of Rho, Rac and Cdc42 in combination is necessary for complete intoxication, or if other substrates are targeted, is not known. It has been found that overexpression of Rho isoforms protects cells from TcdB, suggesting inactivation of all substrates may not be necessary for cellular intoxication. Interestingly, Rho has also been shown to regulate the suppression of apoptosis, so it is not entirely clear whether overexpression of Rho is protective at the substrate inactivation level or prevents events downstream of glucosylation. Additionally, while some TcdB-intoxicating events, such as depolymerization of actin, can be attributed to inactivation of Rho, other processes like apoptosis may be linked to activities other than substrate inactivation. Given TcdB's large size (~270 kD), and broad impact on cell physiology, it is possible the toxin may possess yet undefined activities in addition to glucosylation.

It would be desirable to have a vaccine or therapeutic composition for inhibiting or preventing action of the *C. difficile* TcdB toxin.

SUMMARY OF THE INVENTION

The invention herein contemplates, in one embodiment, a mutant of native *C. difficile* TcdB toxin polypeptide wherein the mutant is substituted at position 395, such that the cysteine at position 395 in the native TcdB toxin has been replaced with another amino acid, for example, a tryptophan residue and wherein the mutant is not cytotoxic (non-toxic). The invention further comprises fragments of the TcdB toxin, which are effective in inhibiting TcdB toxin or are effective as a vaccine, and are non-toxic. The invention further contemplates a vaccine generally applicable to the prevention or treatment of *C. difficile* disease. Additionally, the present invention contemplates a method of inhibiting, modulating, or treating a *C. difficile* or a *C. sordellii* infection in a subject. Further, the present invention contemplates a monoclonal antibody raised against the *C. difficile* TcdB toxin mutant. In addition, the present invention contemplates a method of making an antibody against *C. difficile* TcdB toxin comprising immunizing an animal with an immunogenic amount of the *C. difficile* TcdB toxin mutant. These and other embodiments of the invention will be described further below.

Panel I is a micrograph depicting CHO cells treated with competitive inhibitors; A, PBS alone; B., TcdB alone; C, PA,LFn plus TcdB; D, PA,TcdB$^{1-170}$ plus TcdB; E, PA,TcdB$_{1420}$ plus TcdB; F, PA,TcdB$^{1-500}$ plus TcdB; G, PA,TcdB$_{33-556}$ plus TcdB; H, PA, TcdB$^{C395W}$, plus TcdB; I, PA, TcdB$^{W1024}$plus TcdB; Panel II is a summary of inhibitors capable of blocking TcdB cytopathic effects; ■=TcdB$^{1-420}$; □=TcdB$^{W1024}$; ▨=TcdB$^{C395W}$; ▦=TcdB$^{33-556}$; ▧=TcdB$^{1-500}$.

Figure 4:
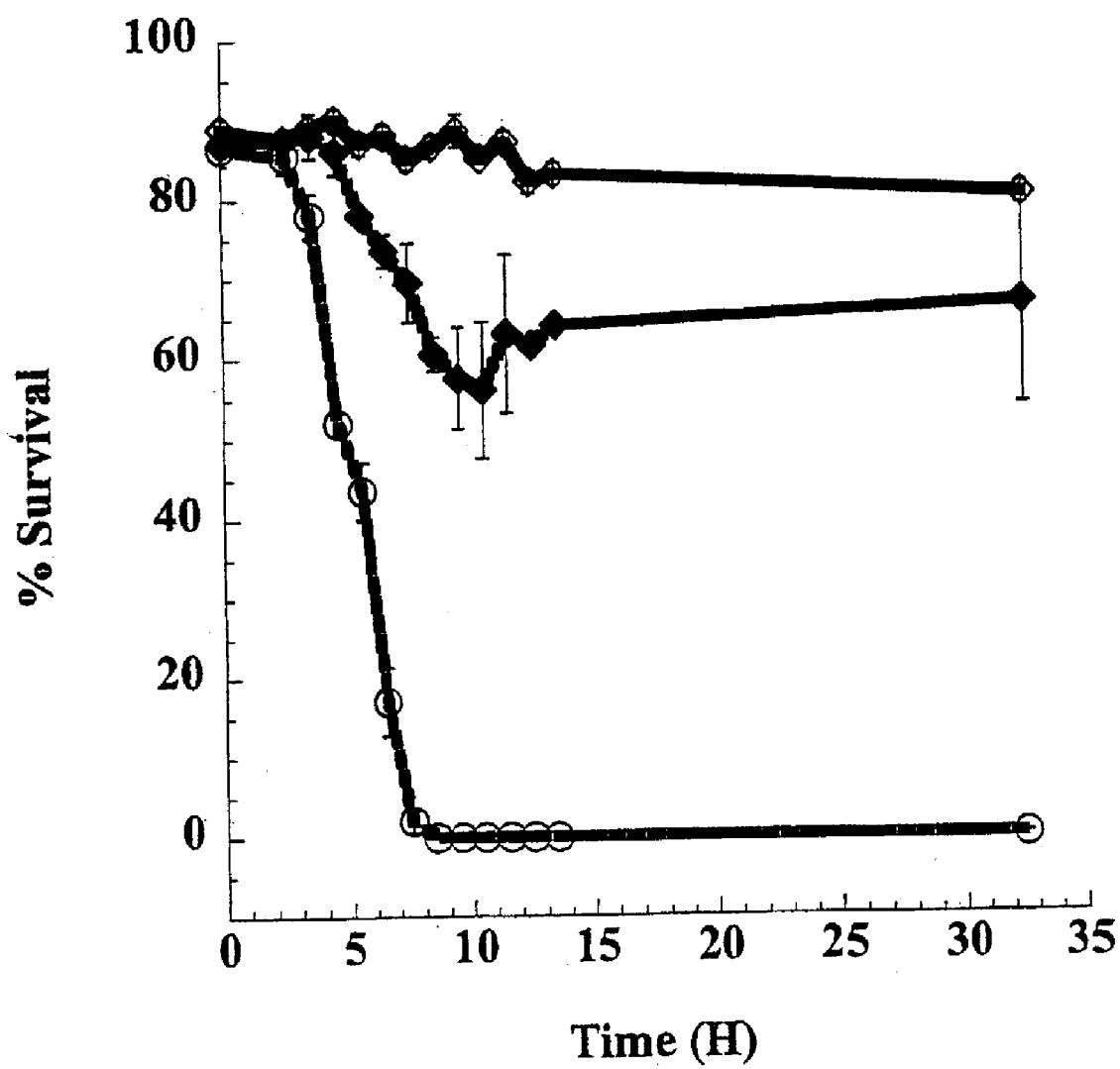

FIG. 4. is a graphical representation depicting sustained inhibition by supplemental treatments with inhibitor. HeLa cells were cotreated with TcdB and TcdB$^{1-500}$ plus PA. During the course of the assay TcdB$^{1-500}$ and PA were added to the cells at 1 h intervals for 12 h. The cells were then followed for 30 h and visualized for cytopathic effects. Open circles TcdB; open diamonds=PA,TcdB$^{1-500}$; closed circles=TcdB$^{1-500}$ plus TcdB.

Figure 5:
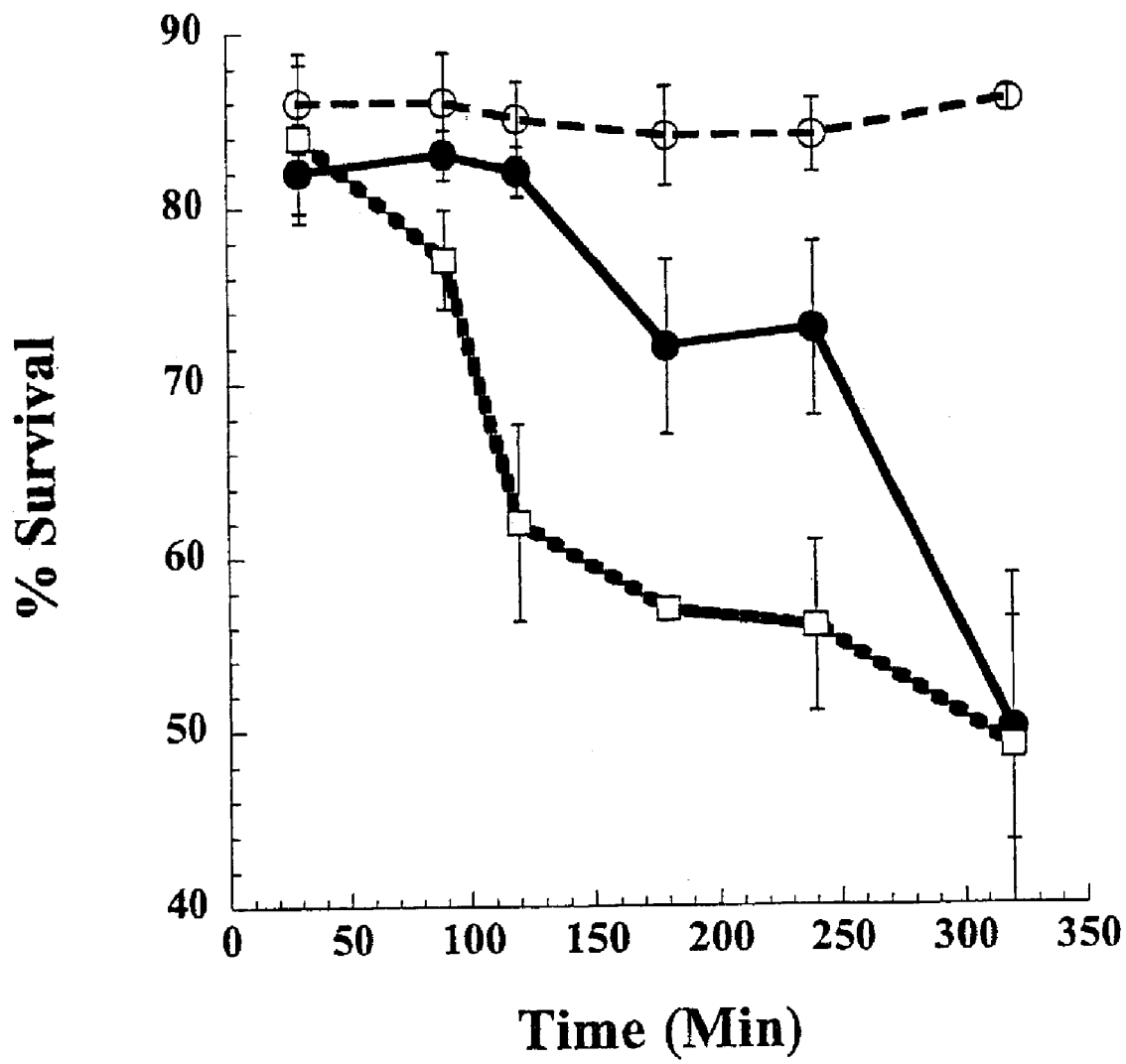

FIG. 5. is a graphical representation depicting the protection of CHO cells expressing TcdB$^{1-556}$. GeneSwitch-CHOpGene/TcdB$^{1-556}$ cells were induced with mifepristone in the presence or absence of TcdB$^{1-500}$ plus PA. Cells were then observed for rounding and cytopathic effects at the indicated time-points. Open Circles=Uninduced Control; Closed Circles=Mifepristone-induced, PA,TcdB$^{1-500}$; Open Squares=Mifepristone-induced control.

Figure 6:
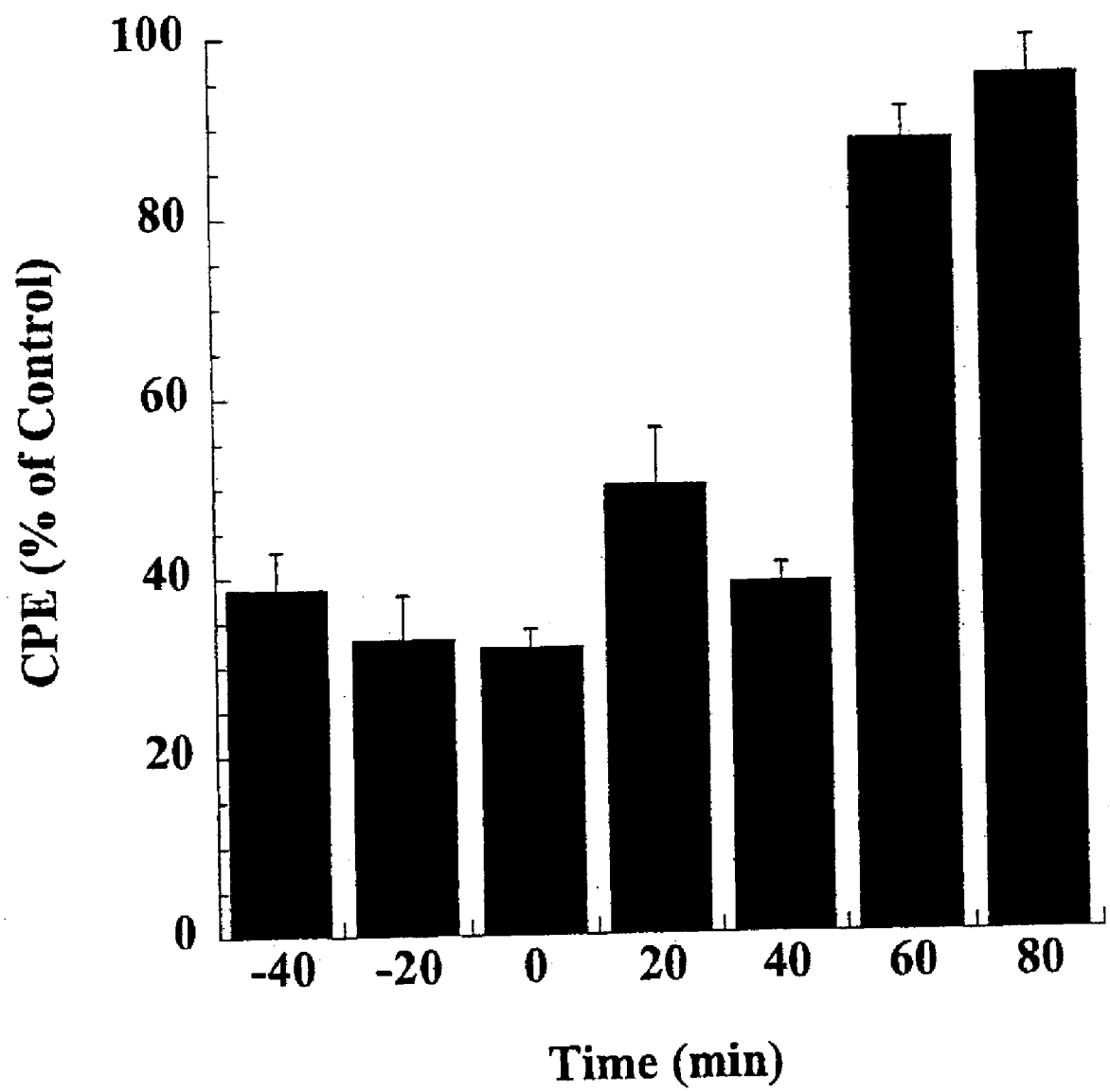

FIG. 6. is a chart demonstrating the inhibitory effects following inhibitor treatments prior to or following treatment with TcdB. In a 96-well plate, HeLa cells were treated with TcdB$^{1-500}$ plus PA at time points prior to or following treatment with TcdB. Cells were amended with inhibitor every 30' and observed for cytopathic effects at 8 h following toxin treatment.

Figure 7:
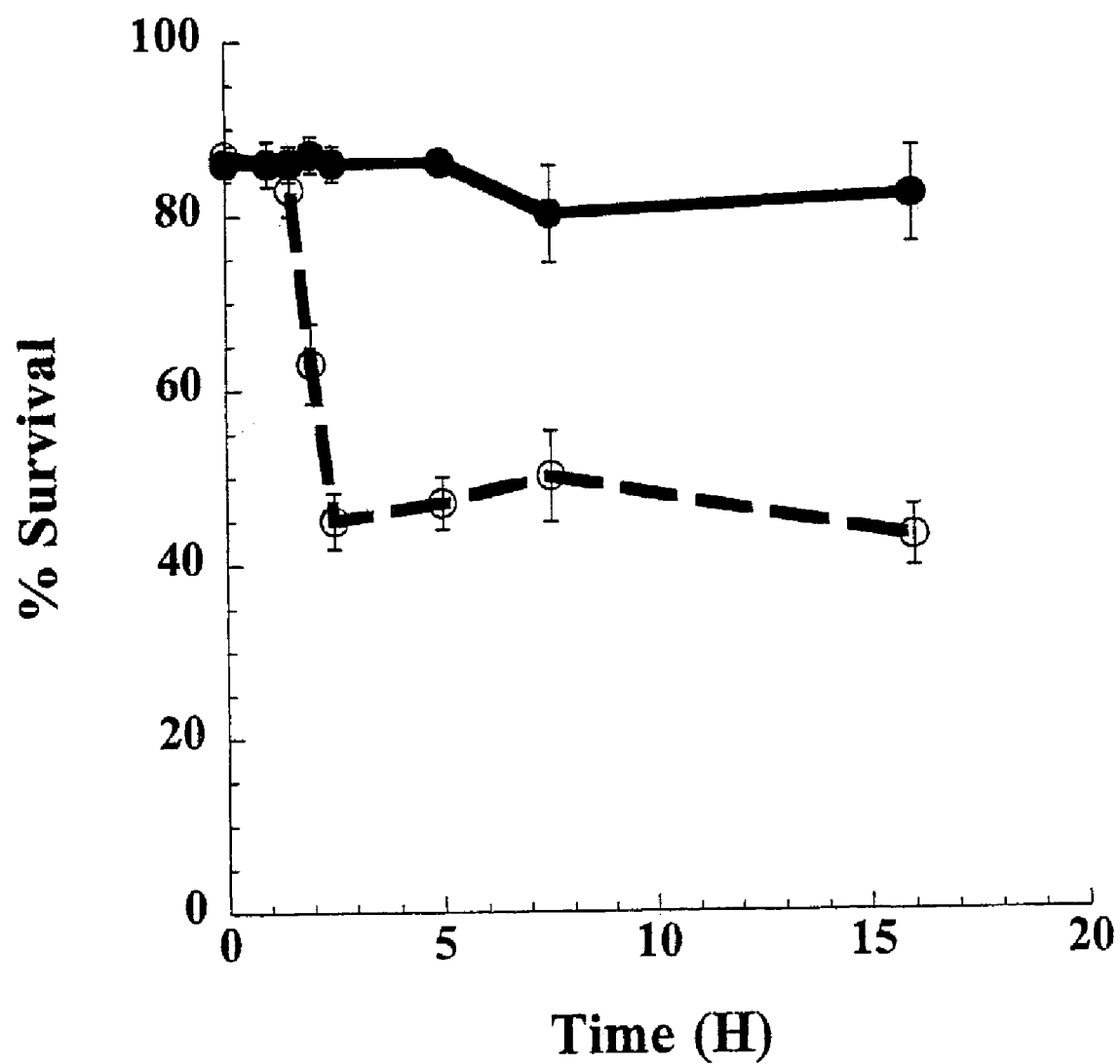

FIG. 7. is a graphical representation depicting TcdB$^{1-500}$inhibition of TcsL cytopathic effects. HeLa cells were treated with TcdB$^{1-500}$ plus PA for 30 min prior to treatment with TcsL. To enhance TcsL cytopathic activity, cells were treated with the toxin using an acid pulse where cells were subjected to TcsL in acid medium (pH 4.0) for 10 min. followed by replacement with neutral medium (pH 7.4) and TcdB$^{1-500}$ plus PA. The cells were amended with inhibitor every 30' for 12 h, then followed for 18 h to determine cytopathic effects. Open circles=TcsL; closed circles=PA, TcdB$^{1-500}$ plus TcsL.

Figure 8:
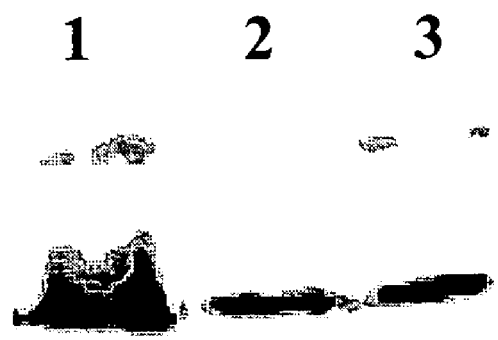

FIG. 8. Differential glucosylation of extracts from cells treated with TcdB plus inhibitor. HeLa cells were plated in T-25 flasks and grown until semiconfluent, then treated with PA, TcdB$^{1-500}$ and TcdB was added to the cells. Three hours after TcdB treatment, cell extracts were collected and subjected to a TcdB glucosylation using [$^{14}$C]UDP-Glucose as cosubstrate. The reactions were subsequently resolved by SDS-PAGE and exposed to film for 48 h. Lane 1=untreated HeLa cells; Lane 2=TcdB-treated cells; Lane 3=TcdB plus inhibitor treated cells.

DETAILED DESCRIPTION OF THE INVENTION

The invention contemplated herein comprises, in a preferred embodiment, non-cytotoxic C. difficile TcdB toxin derivatives and deletions (mutants) which are deficient in at least one specific function required for toxicity and which are effective intracellular inhibitors of native TcdB toxin or are effective in producing immunity against TcdB toxin. The present invention demonstrates that enzymatically inactive fragments of the TcdB enzymatic domain are effective intracellular inhibitors of native TcdB. The present invention comprises purified derivatives (mutants) of C. difficile TcdB toxin which are deficient in glucosyltransferase and glucosylhydrolase activity. The mutants are considered to be useful as a vaccine for both humans and animals.

Examples of animals which may be treated are cattle, chickens, turkeys, ostriches, emu, ducks, horses, donkeys, mules, pigs, sheep, goats antelope, buffalo, llamas, cats, lions, tigers, dogs, bears, guinea pigs, hamsters, chinchillas, mink, ferrets, rodents, parrots, parakeets, peacocks, seals, sea lions, orcas, monkeys, chimpanzees, baboons, orangutans, gorillas, reptiles, and other zoo and livestock animals.

The term "mutant", where used herein, refers to a fragment, point deletion, point substitution, or a deletion of multiple residues of the TcdB protein sequence, and may be encoded by a nucleotide sequence intentionally made variant from a native sequence. The present invention also contemplates nucleotide sequences which encode the mutants.

The mutants of the present invention preferably have at least one substituted amino acid in the enzymatic domain of the TcdB toxin which includes amino acid position 395 of the sequence of the native TcdB toxin as shown in SEQ ID NO: 1.

As noted above, the novel mutants contemplated herein comprise at least one amino acid substitution or deletion of the native C. difficile TcdB toxin. For example, the amino acid at position 395 (also referred to herein as the "critical position") of the amino acid sequence of the native C. difficile TcdB toxin (SEQ ID NO: 1) may be substituted with a different amino acid in the same position.

In particular, the invention comprises mutants wherein the native cysteine at position 395 has been substituted with a tryptophan residue at position 395. However, any amino acid residue which would provide a mutant effective in inhibiting TcdB toxin, and which is not cytotoxic, may be substituted for the cysteine residue at position 395. Examples of other amino acids which may be used to substitute the cysteine residue include alanine, valine, leucine, isoleucine, proline, methionine, phenylalanine, glycine, threonine, tyrosine, asparagine, aspartic acid, glutamine, glutamic acid, lysine, arginine, and histidine. Mutants which are cytotoxic, e.g., a serine-substitute, also comprise the invention, particularly when they are used in a diagnostic assay as described below. Mutants comprising deletions of portions of the enzymatic domain include, for example, a modified C. difficile TcdB toxin having a deletion of amino acid positions 501–556 (SEQ ID NO: 3), 421–556 (SEQ ID NO: 5), 171–556 (SEQ ID NO: 7), or 1–34 (SEQ ID NO: 9) are also contemplated. An especially preferred embodiment comprises a mutant having at least one substitution in the enzymatic domain. The mutants of the present invention preferably have deficient glucosyltransferase and glucosylhydrolase activity compared to the native C. difficile TcdB toxin, and are non-toxic, and in an especially preferred embodiment are antigenic, whereby vaccines produced from them induce anti-TcdB toxin antibodies in vivo as explained in more detail below.

As noted above, it is an object of the present invention to provide novel vaccines comprising the TcdB toxin mutants described herein, or antigenic fragments thereof, which when administered to animals or humans, are capable of inducing production of protective antibodies directed against C. difficile TcdB toxin, thereby providing prophylaxis against infection by C. difficile disease states resulting from such infection, and/or from the TcdB toxin itself. It is a particular aim of the present invention to provide such a vaccine that is relatively safe and simple to produce. Antibodies and antisera raised against the mutants are also capable of use in therapy for at least some, if not all, disease states, in which TcdB toxin is involved.

In further aspects of the present invention there is provided recombinant DNA which encode any proteins, fragments, or amino acid sequences thereof described or claimed herein. Such recombinant DNA is conveniently provided by PCR amplification of the DNA encoding for the desired sequence, using primers targeted at respective ends of the double stranded sequence of which it forms one half, using methods well known to those of ordinary skill in the art.

In a further aspect of the present invention there are provided antisera raised to the mutants, or antigenic fragments thereof, of the invention and antibodies derived therefrom. Furthermore, the present invention provides monoclonal antibodies against the mutants, or antigenic fragments thereof, of the invention and hybridoma cells for production thereof as described in more detail below.

The present invention further contemplates TcdB toxin mutants which have additional substitutions which are merely conservative substitutions of amino acids. By "conservative substitution" is meant the substitution of an amino acid by another one of the same class; the classes according to Table I.

TABLE I

Classes of amino acids suitable for conservative substitution.

| CLASS | AMINO ACID |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His |

As is well known to those skilled in the art, altering any given non-critical amino acid of a protein by conservative substitution may not significantly alter the activity of that protein because the side-chain of the amino acid which is inserted into the sequence may be able to form similar bonds and contacts as the side chain of the amino acid which has been substituted for.

Non-conservative substitutions (outside the classes of Table I) are possible provided that these do not excessively affect the immunogenicity of the polypeptide and/or reduce its effectiveness in inhibiting TcdB toxin.

The polypeptides of the invention may be prepared synthetically, or more suitable, they are obtained using recombinant DNA technology. Thus, the invention further provides a nucleic acid which encodes any of the mutants of TcdB toxin which have at least one substitution and/or deletion as described herein.

Such nucleic acids may be incorporated into an expression vector, such as a plasmid, under the control of a promoter as understood in the art. The vector may include other structures as conventional in the art, such as signal sequences, leader sequences and enhancers, and can be used to transform a host cell, for example a prokaryotic cell such as E. coli or a eukaryotic cell. Transformed cells can then be cultured and polypeptide of the invention recovered therefrom, either from the cells or from the culture medium, depending upon whether the desired product is secreted from the cell or not.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementary may be "partial," in which only some of the nucleic acids' bases are matched according to the base pairing rules. Or, there may be "complete" or "total" complementary between the nucleic acids. The degree of complementary between nucleic acid strands has significant effects on the efficiency and strength of hybridization between nucleic acid strands. This is of particular importance in amplification reactions, as well as detection methods which depend upon binding between nucleic acids.

Nucleic acids of the present invention also include DNA sequences which hybridize to the DNA sequences which encode the mutant polypeptides described herein, or their complementary sequences, under conditions of high or low stringency and which encode proteins having activity against TcdB toxin and/or which preferably can stimulate antibodies against native TcdB toxin.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (expressly entirely incorporated herein by reference). The conditions of temperature and ionic strength determine the "stringency" of the hybridization.

In one embodiment, high stringency conditions are prehybridization and hybridization at 68° C., washing twice with 0.1×SSC, 0.1% SDS for 20 minutes at 22° C. and twice with 0.1×SSC, 0.1% SDS for 20 minutes at 50° C. Hybridization is preferably overnight.

In one example, low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; sigma) and 100 µg/ml denatured salmon sperm DNA] followed by washing in a solution comprising 5×SSPE, 0.1% SDS at 42° C. when a probe of about 500 nucleotides in length is employed.

In another embodiment, low stringency conditions are prehybridization and hybridization at 68° C., washing twice with 2×SSC, 0.1% SDS for 5 minutes at 22° C., and twice with 0.2×SCC, 0.1% SDS for 5 minutes at 22° C. Hybridization is preferably overnight.

In an alternative embodiment, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Souther blotting procedures.

The carrier material is then washed three times each for 15 minutes using 2×SSC, 0.2% SDS preferably at least 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

It is well known in the art that numerous equivalent conditions may be employed to comprise low stringency conditions; factors such as the length and nature (e.g., DNA, RNA, base composition) of the probe and nature of the target (e.g., DNA, RNA, base composition, present in solution or immobilized, etc.) And the concentration of the salts and other components (e.g., the presence or absence of formamide, dextran sulfate, polyethylene glycol) are considered and the hybridization solution may be varied to generate conditions of low stringency hybridization different form, but equivalent to, the above listed conditions. In addition, conditions which promote hybridization under conditions of high stringency (e.g., increasing the temperature of the hybridization and/or wash steps, the use of formamide in the hybridization solution, etc.) are also know in the art.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (e.e., the strength of the association between the nucleic acids) is impacted by such factors as the degree of complementary between the nucleic acids, stringency of the conditions involved, the $T_m$ (melting temperature) of the formed hybrid, and the G:C ration within the nucleic acids. As used herein the term "stringency" is used in reference to the conditions of temperature, ionic strength, and the presence of other compounds such as organic solvents, under which nucleic acid hybridizations are conducted.

As used herein, the terms "cell," "cell line," and "cell culture" are used interchangeably and all such designations include progeny. The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "vector" is used in reference to nucleic acid molecules that transfer DNA segment(s) from one cell to another. The term "vehicle" is sometimes used interchangeably with "vector".

The terms "recombinant DNA vector" as used herein refers to DNA sequences containing a desired coding sequence and appropriate DNA sequences necessary for the expression of the operably linked coding sequence in a particular host organism. DNA sequences necessary for expression in prokaryotes include a promoter, optionally and operator sequence, a ribosome binding site and possibly other sequences. Eukaryotic cells are known to utilize promoters, polyadenylation signals and enhancers. It is not intended that the term be limited to any particular type of vector. Rather, it is intended that the term encompass vectors that remain autonomous within host cells (e.g., plasmids), as well as vectors that result in the integration of foreign (e.g., recombinant nucleic acid sequences) into the genome of the host cell.

The term "expression vector" and "recombinant expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. It is contemplated that the present invention encompasses expression vectors that are integrated into host cell genomes, as well as vectors that remain unintegrated into the host genome.

The terms "in operable combination," "in operable order," and "operably linked," as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The mutants described herein may be expressed in either prokaryotic or eukaryotic host cells. Nucleic acids encoding the mutants may be introduced into bacterial host cells by a number of means including transformation or transfection of bacterial cells made competent for transformation by treatment with calcium chloride or by electroporation. If the mutants are to be expressed in eukaryotic host cells, nucleic acid encoding the protein or toxin of interest may be introduced into eukaryotic host cells by a number of means including calcium phosphate co-precipitation, spheroplast fusion, electroporation, microinjection, lipofection, protoplast fusion, and retroviral infection, for example. When the eukaryotic host cell is a yeast cell, transformation may be affected by treatment of the host cells with lithium acetate or by electroporation, for example.

In a preferred version of the invention, the mutant is characterized as having 50% or less of the glucosyltransferase and glucoslyhydrolase activity of wild type TcdB toxin, as measured by assays described herein. In a more preferred version of the invention, the mutant is characterized as having 30% or less of the glucosyltransferase and glucosylhydrolase activity of wild type TcdB toxin, as measured by assays described herein. In a more preferred version of the invention, the mutant has less than 20% of the glucosyltransferase and glucosylhydrolase activity of wild type TcdB toxin as measured by assays described herein. In a more preferred version of the invention, the mutant has less than 10% of the glucoslytransferase and glucosylhydrolase activity of wild-type TcdB toxin, as measured by assays described herein. More preferably, the mutant has less than 5% of the glucosyltransferase and glucosylhydrolase activity of the wild-type TcdB toxin, as measured by assays described herein. Even more preferably, the mutant has less than 0% of the glucosyltransferase and glucosylhydrolase activity of wild-type TcdB toxin, as measured by assays described herein. More particularly, the invention as contemplated herein is a mutant (mutein) of C. difficile TcdB toxin polypeptide which comprises: (a) a polypeptide having a substitution at position 395 of the amino acid sequence of native C. difficile TcdB toxin, wherein the cysteine at position 395 has been replaced with tryptophan (SEQ ID NO: 11) or with another amino acid; or (b) a modified C. difficile TcdB toxin having a deletion of amino acid positions 501–556 (SEQ ID NO: 3), 421–556 (SEQ ID NO: 5), 171–556 (SEQ ID NO: 7), or 1–34 (SEQ ID NO: 9), and wherein the mutant of (a) or (b) is effective in inhibiting or modulating the cytotoxic effect of C. difficile TcdB toxin or is effective as a vaccine against C. difficile and wherein the mutant is not cytotoxic.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

During analysis of the TcdB enzymatic domain a set of mutants were identifiable which were unable to modify substrate, yet were capable of blocking TcdB cytopathic effects. Herein are described generation and analyses of these mutants and the demonstration that these proteins are potent intracellular inhibitors of TcdB and block glucosylation of a previously undescribed target. These mutants show, for the first time, that a toxin derivative can be used to effectively block the activity of the native toxin within the cell. This inhibitory activity also suggests a new paradigm for a therapeutic approach to treat toxin-based diseases.

Enzymatic and Cytopathic Activity of Mutants

Figure 1:
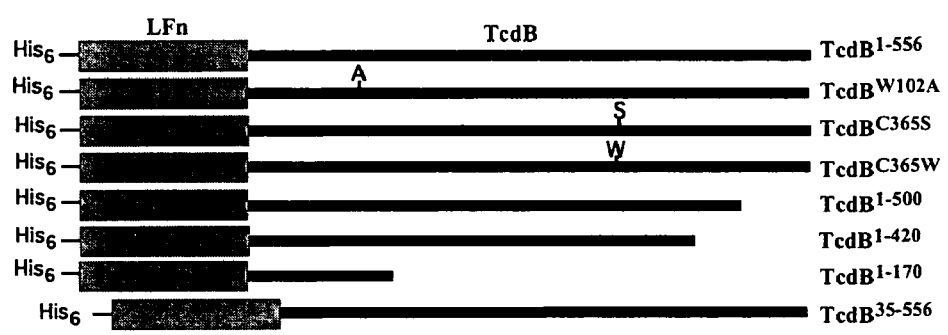
FIG. 1. shows chromatography gels of LFnTcdB deletion and site-directed mutants. Panel A: Overview of deletion and site directed mutants. Deletion mutants were generated by PCR, cloned in-frame with lfn in pET 15b, expressed in *E. coli* BL-21, and subsequently purified by $Ni^{2+}$ affinity chromatography. Site-directed mutants were generated by the Quick-change method, using complementary mutation encoding oligonucleotides, and pLMS200 as template. Panel B: DS-PAGE analysis of his-tagged fusions. Lane 1, Molecular Weight Marker; Lane 2, $TcdB^{W102A}$; Lane 3, $TcdB^{C395W}$; Lane 4, $TcdB^{C395S}$; Lane 5, $TcdB^{35-556}$; Lane 6, $TcdB^{1-170}$; Lane 7, $TcdB^{1-420}$; Lane 8, $TcdB^{1-500}$; Lane 9, $TcdB^{1-556}$; Lane 10, Molecular Weight Marker.
Figure 1:
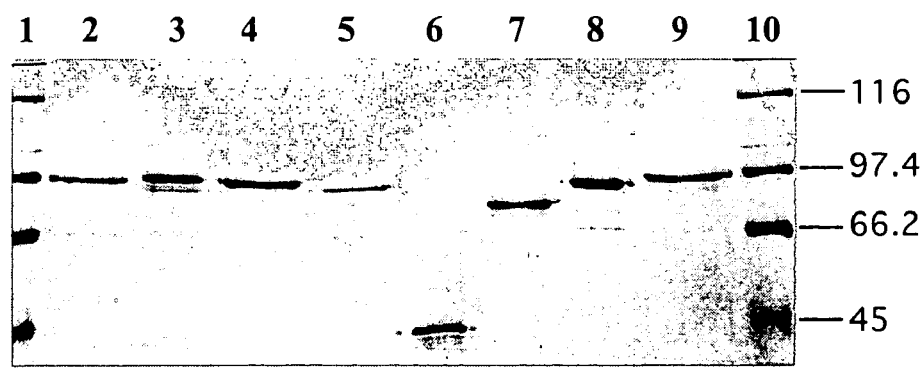

As summarized in FIG. 1, 4 deletion and 3 site-directed mutants in the TcdB enzymatic domain were constructed, cloned and isolated from *E. coli*. The nomenclature for each of these mutants is summarized in panel A of FIG. 1. One site-directed mutant, TcdB$^{W102A}$ wherein the tryptophan at position 102 is substituted with alanine has been previously characterized and served as a control in cytotoxicity and enzymatic assays [Busch, 2000]. Experiments conducted in the present work suggested TcdB$^{1-556}$ (SEQ ID NO: 1) could be inactivated by n-ethylmaleimide (data not shown), indicating a role for the sole cysteine (position 395) in enzymatic activity, thus site-directed mutants TcdB$^{C395S}$, TcdB$^{C395W}$ were produced. Amino-terminal and carboxy-terminal deletions were also generated in an attempt to further identify inactive mutants. Since these mutants lacked receptor binding and translocation domains, the fragments were fused to the cell entry proteins of anthrax lethal toxin. This anthrax toxin derivative consists of anthrax protective antigen (PA), and a truncated form of anthrax lethal toxin (LFn), to which heterologous fusions are made. PA-LFn has been used by several groups for the cytosolic delivery of a variety of proteins, and we previously used this system to deliver TcdB$^{1-556}$ to cultured mammalian cells [Spyres, 2001]. Using this delivery system, the fusions were tested for cytopathic activity and only TcdB$^{1-556}$ and TcdB$^{C395S}$ were cytotoxic (data not shown).

Figure 2:
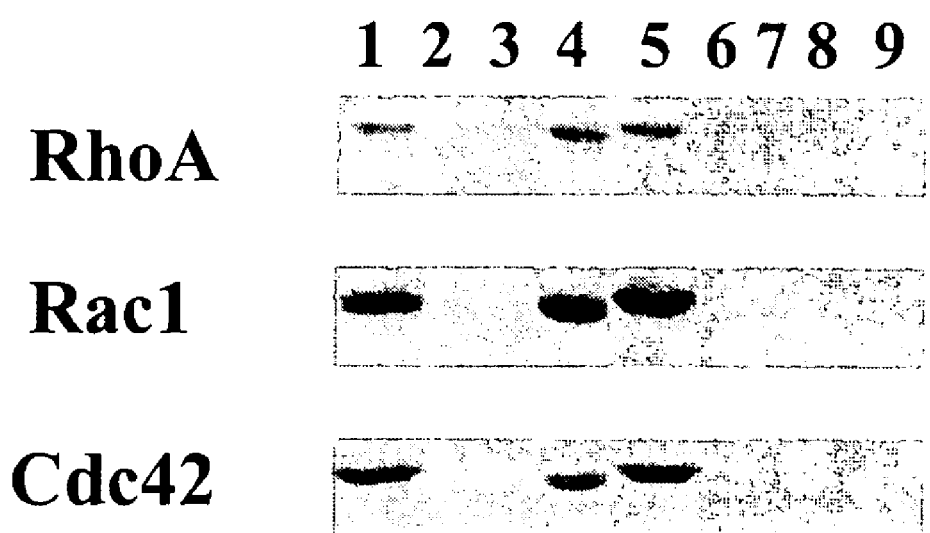
FIG. 2. is a gel depicting glucosylation activity of deletion and site-directed mutants on RhoA, Rac1 and Cdc42. Each mutant and TcdB was tested for glucosylation activity on recombinant substrates GST-RhoA, GST-Rac1 and GST-Cdc42, using [$^{14}$C]UDP-Glucose as cosubstrate. Following a 2 h incubation, the reaction mix was resolved by SDS-PAGE and exposed to film for 48 h. Lane 1, TcdB; Lane 2, $TcdB^{W102A}$; Lane 3, $TcdB^{C395W}$; Lane 4, $TcdB^{C395S}$; Lane 5, $TcdB^{1-556}$; Lane 6, $TcdB^{1-500}$; Lane 7, $TcdB^{1-420}$; Lane 8, $TcdB^{1-170}$; Lane 9, $TcdB^{35-556}$.

To determine if lack of cytotoxicity was due to attenuation of enzymatic activity, mutants were tested for glucosylation of RhoA, Rac1 or Cdc42. As shown in FIG. 2, only TcdB$^{1-556}$, and TcdB$^{C395S}$ glucosylated substrate. In line with earlier reports carboxy-terminal deletions and TcdB$^{W102A}$ were unable to glucosylate substrate. The remainder of the site-directed and deletion mutants were also deficient in glucosylation. Furthermore, this loss of activity was maintained across all of the shared substrates since these same mutants were attenuated in glucosylation of RhoA, Rac1 and Cdc42.

Each mutant was also analyzed for glucosylhydrolase activity using radiolabeled UDP-glucose in the absence of substrate. Fusions were incubated with [$^{14}$C]UDP-glucose and the liberated sugar was separated by anion-exchange chromatography. As shown in Table 1, even with extended (16 h) incubation glucosylhydrolase activity was significantly reduced for all enzymatically inactive mutants. Without wishing to be constrained by theory, the absence of substrate modification by these mutants could be accounted for, at least in part, by defective hydrolase activity.

TcdB Mutants as Inhibitors of Native Toxin

Since the inactive mutants could be effectively delivered to the cytosol of cells via the PA, LFn system, we were presented with the unique opportunity to examine the effects these mutants might have when administered in combination with wild-type TcdB. Thus, HeLa cells were treated with TcdB in the presence or absence of PA plus each attenuated mutant. As shown in FIG. 3(I), PA-delivered TcdB$^{1-500}$, TcdB$^{1-420}$, TcdB$^{W102A}$, TcdB$^{C395W}$, or TcdB$^{35-556}$, attenuated TcdB cytopathic effects suggesting the mutants had an antagonistic impact on TcdB intoxication. The inhibitor effects were dependent on the presence of inactive enzymatic domain mutants since PA-LFn alone did not inhibit TcdB.

Figure 3:
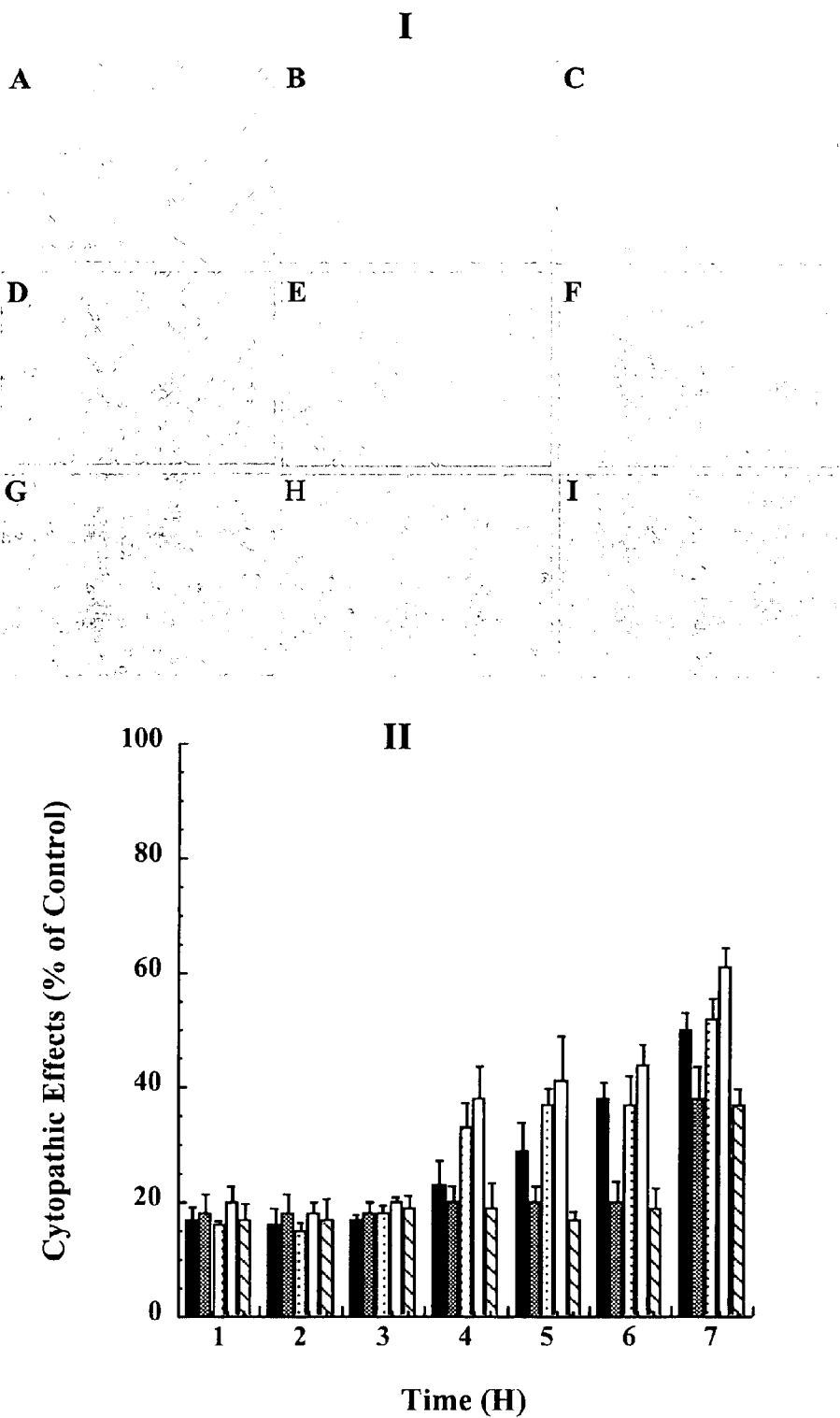
FIG. 3. shows inhibition of TcdB cytopathic effects by TcdB mutants. HeLa cells were cotreated with TcdB and each TcdB fusion plus PA. The cells were followed for 7 h and cytopathic effects were determined by visualization.

It was clear from the results in FIG. 3(II), that approximately 7 h after delivery of inhibitory fragments to the TcdB treated cells that the protective effect began to decrease. This observation suggested that the inhibitory effect of the enzymatically inactive mutants has a limited lifetime. To address this possibility, the initial competition was set-up as before and the inhibitor (TcdB$^{1-500}$) was added to the cells at 1 h time intervals during the course of the assay. As shown in FIG. 4, using this approach greater than 50% of the cells demonstrated no cytopathic effects and appeared to be protected from the wild-type toxin during the course of the assay (>30 h). Hence, continued administration maintained the protective effect against TcdB. Continued addition of the inhibitor after 12 h, did not improve or change the inhibition of TcdB, suggesting TcdB had lost activity or that the accumulated inhibitor was in sufficient excess so that its protective effect was extended.

Inactive Mutants Protect CHO Cells Expressing TcdB$^{1-556}$

The fact that the TcdB inhibitors lack native translocation and receptor binding domains suggested that inhibition occurred within the cytosol. However, inhibition at the cell surface could not be formally excluded since cell surfacing-interacting regions of TcdB have not been fully elucidated. To determine if inhibition of TcdB was occurring within the cytosol, a CHO cell line capable of inducible expression of TcdB$^{1-556}$ was generated. A tightly regulated expression system, pSwitch, was selected which allows expression only in the presence of the hormone mifepristone. GeneSwitch-CHOpGene/TcdB$^{1-556}$ cells showed early toxic effects, such as rounding, at around 4 h following addition of mifepristone and were no longer viable by 24 h. To test the inhibitor on these cells, mifepristone was added to the cells and inhibitor was added 2 h later and subsequently added every 30 min for an additional 3 h. As shown in FIG. 5, mifepristone treated GeneSwitch-CHOpGene/TcdB$^{1-556}$ cells were protected from the effects of TcdB$^{1-556}$ when the inhibitor was added at 2 h following induction. The inhibitor clearly slows the cytopathic activity of these cells following induction. Cells eventually show cytopathic effects similar to that control since the cell continues to express TcdB$^{1-556}$. These results demonstrate that the inhibitor is capable of blocking TcdB intoxication at a site within the cell.

TcdB-Inhibitors as Tools to Dissect the Time-Course of Posttranslocation Events

In earlier studies we reported on the time-course of entry by TcdB, based on results from lysosomotropic inhibitor assays [Qa'Dan, 2000]. The inhibitors now provided a reagent to determine the time-course of events occurring after translocation into the cytosol. At a given time-point, if intoxication events have been initiated, then addition of the inhibitor should no longer have an effect. In this experiment cells were pretreated with the inhibitor or treated with the inhibitor at time-points following TcdB treatment. As shown in FIG. 6, protection occurs in cells when the inhibitor is added as early as 40 min before treatment with TcdB. Protection also occurs when the inhibitor is added up 40 min after treatment with TcdB. Only when the inhibitor is added over 40 min prior to treatment with TcdB or over 40 min after treatment with TcdB is there a noticeable cytopathic effect. Given that cell entry takes approximately 20 min, these results suggested intoxication events require at least a 40 min time period after translocation to initiate cytotoxic effects.

Inhibition of Intoxication by *C. sordellii* Lethal Toxin (TcsL)

A variety of events, including substrate related and substrate unrelated, could occur during the 40 min posttranslocation time-period. If the inhibitor blocked processes unrelated to substrate interaction, we suspected the mutant might block another highly related LCT, which does not share similar substrate targets with TcdB. An ideal candidate for this experiment was TcsL, which is closely related to TcdB, yet modifies a different set of Ras proteins including Ras, and Ral. TcsL does share Rac as a common substrate with TcdB. We tested the TcdB inhibitor's ability to block TcsL intoxicaion. In recent work we reported that acid pH enhances TcsL entry [Qa'Dan, 2001], so the initial treatment with TcsL was carried out by providing an extracellular acid pulse to TcsL. In this assay cells were pretreated with the inhibitor, then acid-pulse treated with TcsL, and subsequently treated with additional inhibitor during the time-course of the assay. As can be seen in FIG. 7, TcdB$^{1-500}$ was also able to block the activity of TcsL. Similar to results with TcdB, the inhibitor was capable of reducing TcsL's cytopathic effects by almost 50%. These results suggested the TcdB inhibitor was blocking LCT intoxication events that might not be related to substrate targeting or that blocking a single target was sufficient to prevent toxic effects.

Effects of Inhibitor on Substrate Glucosylation in Cultured Cells

The results from the TcsL inhibition assay suggested the inhibitor prevented toxin-specific activities that might not be related to targeting Rho, Rac and Cdc42. For this reason it was important to determine if the inhibitor prevented glucosylation of these substrates during TcdB intoxication. Thus, a set of differential glucosylation reactions were carried out that involved examining extracts from cells treated with TcdB, or treated with TcdB plus the inhibitor, for a decrease in substrate that could be glucosylated. As shown in FIG. 8 using a minimal intoxicating dose of TcdB, cells showed a relatively equal amount of Rho substrate that could be glucosylated from both TcdB-treated and TcdB-plus-inhibitor treated cells. While there did not appear to be a difference in targeting of Rho, Rac or Cdc42 there was a change in the ability to glucosylate a second protein that migrated at a size larger than the Rho proteins. The larger protein was below the level of detection in extracts from TcdB treated cells yet this protein was glucosylated in extracts from cells treated with TcdB plus the inhibitor. These results further suggest the inhibitor prevents an LCT activity other than glucosylation of Rho, Rac and Cdc42.

Attenuated mutants of TcdB inhibit wild-type toxin at an intracellular site. To our knowledge this is the first example of an approach that blocks the activity of an intracellular bacterial toxin within the cytosol of intoxicated cells. This inhibitory effect also suggests some yet undefined aspects of TcdB. Clearly, while unable to modify substrate, the mutants carry out functions within the cytosol, which allow inhibition. The exact mode of inhibition is not clear; however, the preliminary evidence indicates the inhibitor prevents glucosylation of a substrate other than Rho, Rac or Cdc42. This is a feasible possibility since some of the inhibitors do not encompass the region of TcdB reported to interact with Rho, Rac and Cdc42. Work by Hofmann et al. [Hofmann, 1998] using chimeric derivatives between the enzymatic domains of TcsL and TcdB, suggested residues 365–516 conferred substrate specificity. Our deletion analysis shows residues 1–420 are able to inhibit TcdB intoxication, while the 1–170 deletion has no inhibitory effect. Finally, the mutants also inhibit TcsL, which shares only one substrate, Rac, with TcdB. If inhibition were due to Rho, Rac and Cdc42 interaction then the inhibitor should be less effective on TcsL, but it is not. The amino terminal domains of these two proteins are homologous (78% homology) and could share activities, and yet undefined common substrates.

Experimental Procedures

Tissue Culture, Bacterial Strains and Chemical Reagents

Human cervical adenocarcinoma cells American Type Culture Collection (ATCC) Manassas, Va. CCL-2 (HeLa) were grown in supplemented RPMI 1640 (RP-10) [Starnbach, 1994] with 10% fetal bovine serum at 37° C. in a humid atmosphere with 7% $CO_2$. *Clostridium difficile* strain VPI 10463, and *Clostridium sordellii* strain 9714 were obtained from ATCC and used as a source of culture supernatant, genomic DNA, TcdB and TcsL. All reagents were of molecular biology grade and were purchased from Sigma Chemical Co., St. Louis, Mo. unless otherwise noted.

Construction of Recombinant LFn-TcdB Fusions

The region encoding for the enzymatic domain of TcdB i.e., TcdB nucleotides 1–1668 (SEQ ID NO:2)) was genetically fused to lfn, cloned expressed and purified in *E. coli* as previously described [Spyres, 2001]. Using a similar approach, four other fusions of LFnTcdB were also constructed. Briefly, fragments encoding regions TcdB$^{1-500}$ (SEQ ID NO: 3 encoded by nucleotides 1–1500 (SEQ ID NO: 4)), TcdB$^{1-420}$ (SEQ ID NO: 5 encoded by nucleotides 1–1260 (SEQ ID NO: 6)), TcdB$^{1-170}$ (SEQ ID NO: 7 encoded by nucleotides 1–510 (SEQ ID NO: 8)), and TcdB$^{35-556}$ (SEQ ID NO: 9 encoded by nucleotides 103–1668 (SEQ ID NO: 10)), were PCR amplified and cloned into the BamHI site of pABII [Spyres, 2001] to make the plasmids pLMS201, pLMS202, pLMS204, and pLMS301 respectively. Plasmids were transformed into *E. coli* XL 1-blue (Stratagene) and candidate clones were sequenced, then transformed into *E. coli* BL-21 Star (INVITROGEN) for expression.

Site-directed mutants were generated using Pfu Turbo DNA polymerase and the QuickChange mutagenesis approach (Stratagene). Oligonucleotides for generation of TcdB1-556$^{C395S}$ (SEQ ID NO: 11, where Xaa at position 395 is serine) were GTTTACTATTAAATTGCTAGAATAT-GAGTCTTTCACAG (sense) (SEQ ID NO: 13), CTGT-GAAGACTCATATTCTAGCAATTTAATAGTAAAAC (antisense) (SEQ ID NO: 14); TcdB1-556$^{C395W}$ (SEQ ID NO: 11, where Xaa at position 395 is tryptophan) GTTT-TACTATTAAATTGCTACCTATGAGTCTTTCACAG (sense) (SEQ ID NO: 15), CTGTGAAAGACTCATATTG-GAGCAATTTAATAGTAAAAC (antisense) (SEQ ID NO: 16); TcdB1-556$^{W1024}$ (SEQ ID NO: 12) AAAAATTTA-CATTTTGTTGCTATTGGAGGTCAA (sense) (SEQ ID NO: 17), TTGACCTCCAATAGCAACAAAATG-TAAATTTTT (antisense) (SEQ ID NO: 18). Mutants were selected in E. coli XLI-blue and confirmed by sequencing, followed by transformation into E. coli BL-21 Star for expression.

Purification of Recombinant Proteins and TcdB

Expression of LFnTcdB fusions was induced with 0.2 mM iso-propyl-β-D-thiogalactopyranoside in log phase (OD$_{600}$ 0.8) cultures at 16° C. Cells were harvested by centrifugation at 8700×g, resuspended in binding buffer (5 mM imidazole, 500 mM NaCl, 20 mM Tris-HCl, pH7.9) supplemented with a protease inhibitor cocktail containing 4-(2-aminoethyl)benzenesulfonyl fluoride, phosphoramidon, pepstatin A, bestatin, and E-64 and lysed by sonication. LFnTcdB fusion proteins were isolated using nickel 900 cartridges following the manufacturer's instructions (NOVAGEN). As a second purification step, proteins were fractionated on a high-resolution anion exchange (MONO-Q) column (Amersham Pharmacia). Recombinant PA was isolated from E. coli BL-21, harboring the plasmid, pSRB/ET-15b-PA (a generous gift from Steven Blanke), as previously described [Whilhite, 1998]. TcdB and TcsL were purified as previously described [Qa'Dan, 2000]. Recombinant clones of RhoA, Rac1, and Cdc42 (a generous gift of Alan Hall) were expressed and purified as previously described [Spyres, 2001].

Glucosylhydrolase/Glucosylation Assays

Glucosylation reactions were carried out as previously described [Spyres, 2001]. Glucosylhydrolase assays were carried out in a reaction mix containing 50 mM n-2hydroxyethylpiperazine-n'-2-ethane sulfonic acid, 100 mM KCl, 1 mM MnCl$_2$, 1 mM MgCl$_2$, 100 μg/ml BSA, 0.2 mM GDP, 40 μM [$^{14}$C]UDP-glucose (303 Ci/mol; ICN Pharmaceuticals), 100 μM UDP-glucose and 3 pmol of TcdB or 10 pmol of each fusion protein. The assay was allowed to incubated overnight at 37° C. and similar to a previously described protocol [Ciesla, 1998], the cleaved glucose was separated using AG1-X2 anion exchange resin and counted in a liquid scintillation counter.

Assay for Cytopathic Effects and Inhibitor Assays

To determine the cytopathic activity of each fusion and site-directed mutant, HeLa cells were plated in 96 well microtiter plates (3×10$^4$ cells/well) and allowed to incubate overnight. The following day the cells were treated with 30 pmol of each fusion plus 8.5 pmol of PA and observed for 48 h for signs of cytopathic effects. For inhibition assays, HeLa cells were plated as before and treated with 4 pmol of the appropriate LFnTcdB fusion plus 8.5 pmol of PA in a final volume of 100 μl. At the same point the cells were cotreated with 80 fmol of TcdB and observed for cytopathic effects. In a second competition assay, 30 pmol of TcdB$^{1-500}$ plus 8.5 pmol of PA were added to cells in a final volume of 100 μl and allowed to incubate 30 min, at which point 20 fmol of TcdB was added to the cells. Following the initial treatment, 30 pmol of TcdB$^{1-500}$ and 8.5 pmol of PA were added every 30 min for the first 90 min and every hour thereafter up to 12 h. The cells were observed for cytopathic effects for an additional 18 h. Similar competition assays were carried out using 2 pmol of TcsL. For inhibition assays with TcsL, cells were subjected to a brief acid-pulse, which enhances cytotoxic activity for this toxin. For TcsL competition, cells were pretreated with TcdB$^{1-500}$ and PA for 30 min at which point cells were treated with TcsL via an acid pulse as previously described [Qa'Dan, 2001]. The cells were then amended with 30 pmol of TcdB$^{1-500}$, 8.5 pmol of PA every 30 min up to 12 h and followed for 16 h. For differential glucosylation assays, HeLa cells semi-confluent (1×10$^6$) were first treated with 325 pmol of PA and 300 pmol of TcdB$^{1-500}$ followed by treatment with 50 fmol of TcdB in a final volume of 10 ml. Following 3 h of treatment cells were washed 3 times in ice-cold PBS, scraped and extracts were prepared as previously described [Spyres, 2001]. Using each extract as target substrate, glucosylation reactions were identical to those previously described with changes only to reaction volume (30 μl) and amount of substrate (80 μg).

Generation of TcdB-expressing CHO Cells

A DNA sequence coding for the enzymatic domain of TcdB (amino acids 1 to 556) placed downstream and in-frame with a Kozak sequence (GNNATGG) was cloned between the HindIII and EcoRI sites of plasmid pGene/V5-His version B (INITROGEN) multiple cloning site. The recombinant plasmid was linearized with SapI and introduced into GeneSwitch-CHO cells (INITROGEN) by lipofection according to the protocol supplied with the LIPOFECTAMINE PLUS Reagent Kit (Gibco Life Technologies). Stably transfected cells were selected for on selective growth medium consisting of complete F-12 (HAM) medium plus zeocin (300 mg/ml) and hygromycin (100 mg/ml) by feeding the cells with selective medium every 3 to 4 days until foci could be seen. Antibiotic resistant cells were treated with trypsin (0.25%) solution for 3 min, diluted with 5 volumes of complete F-12 (HAM) medium and harvested by centrifugation at 250×g for 5 min. Cells were then resuspended in complete F-12 (HAM) medium, and diluted to a final cell density of five cells per ml. One hundred microliters of cell suspension was used to seed the wells of two 96-well plates. Only wells containing single foci were subcultured on selective medium in 12 and 24-well plates. Expression of TcdB was induced in the different cell lineages of transfected CHO cells by the addition of mifepristone (10$^{-8}$M), to the selective medium. GeneSwitch-CHOpGene/TcdB1-556 a lineage of transfected cells showing nearly. 100% rounding in 24 h in the presence of mifepristone was identified and chosen for the experiments reported herein.

Statistical Analysis

Results were analyzed using the statistical software component of Excel 2001. Sample variations are reported as standard deviation from the mean, and significance was confirmed by student's T-test (p<0.05).

Utility

Since the preferred embodiments of the mutants contemplated herein are inactive, and therefore are not lethal, but are effective in binding to native TcdB toxin, they will make excellent therapeutics or vaccines against C. difficile toxins or infections in their pure and partially pure forms. The mutant toxin may be therapeutically administered to inhibit active TcdB in subjects having existing C. difficile infections or circulating TcdB toxin, for example, for treating or inhibiting diarrhea or pseudomembranous colitis.

The administration of a human vaccine comprising one or more of the mutants described herein is applicable to the prevention or treatment of a C. difficile infection in a human or animal. The vaccine may be administered by epicutaneous injection, subcutaneous injection, intramuscular injection, interdermal injection (injection by infusion), sustained-release repository, aerosolization, parenteral delivery, inoculation into an egg, and the like, by known techniques in the art. Although this approach is generally satisfactory, other routes of administration, such as i.v. (into the blood stream) may also be used in a manner known to those of ordinary skill in the art. In addition, the vaccine can be given together with adjuvants and/or immuno-modulators to boost the activity of the vaccine and the subject's response, the subject being a human or animal as described elsewhere herein.

The amount of protein in each therapeutic or vaccine dose can be selected as an amount which induces an antitoxin or immunoprotective response without significant, adverse side effects. Such amount in a vaccine will vary depending upon which specific immunogen is employed, how it is presented, and the size of the subject treated. Generally, it is expected that each therapeutic or immunogenic dose of the protein will comprise 0.1–1000 µg/kg of weight of the subject, preferably 0.2–100 µg/kg, and most preferably 1–10 µg/kg. An optimal amount for a particular vaccine can be ascertained by standard studies involving observation of appropriate immune responses in subjects. Following an initial vaccination, subjects may receive one or several booster immunization adequately spaced. Therapeutic doses for inhibiting TcdB toxin may also be from 10 µg–1 mg/kg, for example.

Accordingly in one aspect, the invention provides a method of treatment comprising administering an effective amount of a vaccine of the present invention to a subject. The vaccine formulations of the present invention may be used for both prophylactic and therapeutic purposes. The vaccine compositions of the present invention can be formulated according to known methods of preparing pharmaceutically useful compositions, whereby these materials are combined in a mixture with a pharmaceutically acceptable carrier vehicle. Suitable vehicles and their formulation are described, for example, in *Remingtons' Pharmaceutical Sciences*, (Mack Publishing Co., 1980).

The TcdB toxin mutants can be administered in combination with a pharmaceutical carrier compatible with the protein and the subject. Suitable pharmacological carriers include, for example, physiological saline (0.85%), phosphate-buffered saline (PBS), Tris hydroxymethyl aminomethane (TRIS), Tris-buffered saline, and the like. The protein may also be incorporated into a carrier which is biocompatible and can incorporate the protein and provide for its controlled release or delivery, for example, a sustained release polymer such as a hydrogel, acrylate, polylactide, polycaprolactone, polyglycolide, or copolymer thereof. An example of a solid matrix for implantation into the subject and sustained release of the protein antigen into the body is a metabolizable matrix, as known in the art.

Adjuvants may be included in the vaccine to enhance the immune response in the subject. Such adjuvants include, for example, aluminum hydroxide, aluminum phosphate, Freund's Incomplete Adjuvant (FCA), liposomes, ISCOM, and the like. The vaccine may also include additives such as buffers and preservatives to maintain isotonicity, physiological pH and stability. Parenteral and intravenous formulations of the vaccine may include an emulsifying and/or suspending agent, together with pharmaceutically-acceptable diluents to control the delivery and the dose amount of the vaccine.

Factors bearing on the therapeutic or vaccine dosage include, for example, the age and weight of the subject. The range of a given dose is about 25–5000 µg of the purified mutant receptor protein per ml, preferably about 100–1000 µg/ml preferably given in about 0.1–5 ml doses. The vaccine or therapeutic should be administered to the subject in an amount effective to ensure that the subject will develop an immunity to protect against a *C. difficle* infection or a therapeutic response against a current *C. difficile* infection. For example, a vaccine for immunizing an about 5-lb. piglet against *C. difficile* would contain about 100–5000 µg protein per ml, preferably given in 1–5 ml doses. The immunizing dose would then be followed by a booster given at about 21–28 days after the first injection. Preferably, the vaccine is formulated with an amount of the TcdB toxin mutant effective for immunizing a susceptible subject against an infection by more than one strain *C. difficile*.

The present invention further contemplates a monoclonal antibody raised against the *C. difficile* TcdB toxin mutant. The monoclonal antibody may be prepared by a method comprising immunizing a suitable animal or animal cell with an immunogenic *C. difficile* TcdB toxin mutant to obtain cells for producing an antibody to said mutant, fusing cells producing the antibody with cells of a suitable cell line, and selecting and cloning the resulting cells producing said antibody, or immortalizing an unfused cell line producing said antibody, e.g. by viral transformation, followed by growing the cells in a suitable medium to produce said antibody and harvesting the antibody from the growth medium in a manner well known to those of ordinary skill in the art. The recovery of the polyclonal or monoclonal antibodies may be preformed by conventional procedures well known in the art, for example as described in Kohler and Milstein, *Nature* 256, 1975, p. 495.

In a further aspect, the invention relates to a diagnostic agent which comprises a monoclonal antibody as defined above. Although in some cases when the diagnostic agent is to be employed in an agglutination assay in which solid particles to which the antibody is coupled agglutinate in the presence of a *C. difficile* toxin in the sample subjected to testing, no labeling of the monoclonal antibody is necessary, it is preferred for most purposes to provide the antibody with a label in order to detect bound antibody. In a double antibody ("sandwich") assay, at least one of the antibodies may be provided with a label. Substances useful as labels in the present context may be selected from enzymes, fluorescers, radioactive isotopes and complexing agents such as biotin. In a preferred embodiment, the diagnostic agent comprises at least one antibody covalently or non-covalently bonded coupled to a solid support. This may be used in a double antibody assay in which case the antibody coupled to the solid support is not labeled. The solid support may be selected from a plastic, e.g. latex, polystyrene, polyvinylchloride, nylon, polyvinylidene difluoride, cellulose, e.g. nitrocellulose and magnetic carrier particles such as iron particle coated with polystyrene.

The monoclonal antibody of the invention may be used in a method of determining the presence of *C. difficile* TcdB toxin in a sample, such as blood, plasma, or serum, the method comprising incubating the sample with a monoclonal antibody as described above and detecting the presence of bound toxin resulting from said incubation. The antibody may be provided with a label as explained above and/or may be bound to a solid support as exemplified above.

In a preferred embodiment of the method, a sample desired to be tested for the presence of *C. difficile* is incubated with a first monoclonal antibody coupled to a solid support and subsequently with a second monoclonal or polyclonal antibody provided with a label. In an alternative embodiment (a so-called competitive binding assay), the sample may be incubated with a monoclonal antibody coupled to a solid support and simultaneously or subsequently with a labeled *C. difficile* TcdB toxin competing for binding sites on the antibody with any toxin present in the sample. The sample subjected to the present method may be any sample suspected of containing a *C. difficile* TcdB toxin. Thus, the sample may be selected from bacterial suspensions, bacterial extracts, culture supernatants, animal body fluids (e.g. serum, colostrum or nasal mucous) and intermediate or final vaccine products.

Apart from the diagnostic use of the monoclonal antibody of the invention, it is contemplated to utilize a well-known ability of certain monoclonal antibodies to inhibit or block the activity of biologically active antigens by incorporating the monoclonal antibody in a composition for the passive immunization of a subject against diseases caused by *C. difficile* producing a TcdB toxin, which comprises a monoclonal antibody as described above and a suitable carrier or vehicle. The composition may be prepared by combining a therapeutically effective amount of the antibody or fragment thereof with a suitable carrier or vehicle. Examples of suitable carriers and vehicles may be the ones discussed above in connection with the vaccine of the invention. It is contemplated that a *C. difficile*-specific antibody may be used for prophylactic or therapeutic treatment of a subject having a *C. difficile* infection or a subject which may potentially incur a *C. difficile* infection.

A further use of the monoclonal antibody of the invention is in a method of isolating a *C. difficile* TcdB toxin, the method comprising adsorbing a biological material containing said toxin to a matrix comprising an immobilized monoclonal antibody as described above, eluting said toxin from said matrix and recovering said toxin from the eluate. The matrix may be composed of any suitable material usually employed for affinity chromatographic purposes such as agarose, dextran, controlled pore glass, DEAE cellulose, optionally activated by means of CNBr, divinylsulphone, etc. in a manner known per se.

In a still further aspect, the present invention relates to a method of determining the presence of antibodies against *C. difficile* TcdB toxin in a sample, the method comprising incubating the sample with *C. difficile* TcdB toxin and detecting the presence of bound antibody resulting from incubation. A diagnostic agent comprising the TcdB toxin used in this method may otherwise exhibit any of the features described above for diagnostic agents comprising the monoclonal antibody and be used in similar detection methods although these will detect bound antibody rather than bound TcdB toxin as such. The diagnostic agent may be useful, for instance as a reference standard or to detect anti-toxin antibodies in body fluids, e.g. serum, colostrum or nasal mucous, from subjects exposed to the toxin or *C. difficile*.

The monoclonal antibody of the invention may be used in a method of determining the presence of a *C. difficile* toxin, in a sample, the method comprising incubating the sample with a monoclonal antibody and detecting the presence of bound toxin resulting from said incubation.

The present invention further contemplates a nucleic acid sequence encoding a *C. difficile* TcdB toxin mutant wherein the nucleic acid sequence is a cDNA similar to a cDNA which encodes native *C. difficile* TcdB toxin, but differs therefrom only in having instead a substituted codon which encodes the substituted amino acid or amino acids in the mutant TcdB toxin, as defined herein, and wherein the substituted codon is any codon known to encode the substitute amino acid residue. The mutant TcdB toxin described herein may be produced by well-known recombinant methods using cDNA encoding the mutant TcdB toxin, the cDNA having been transfected into a host cell in a plasmid or other vector.

In particular, the present invention contemplates any antigenic *Clostridium difficile* TcdB toxin mutant wherein the TcdB toxin mutant lacks the toxicity of a native *C. difficile* TcdB toxin.

As noted above, the invention contemplates a vaccine for use in immunizing a human or an animal against an infection by *Clostridium difficile*, the vaccine comprising a purified non-toxic *C. difficile* TcdB toxin mutant.

Alternatively, the present invention contemplates a method for immunizing a subject against an infection by *Clostridium difficile* by administering an effective quantity of a vaccine comprising at least one purified non-toxic *C. difficile* TcdB toxin mutant as defined elsewhere herein. In this method, the vaccine may be administered by epicutaneous injection, subcutaneous injection, intramuscular injection, interdermal injection, intravenous injection, sustained-release repository, aerosolization, parenteral delivery, or inoculation into an egg. In one embodiment of the method, the vaccine induces an effective antibody titer to prevent or eliminate the infection without administration of a booster of the vaccine.

The present invention further contemplates a serum for treating a subject with an existing a *Clostridium difficile* infection comprising antibodies against a *C. difficile* TcdB toxin wherein the antibodies are raised against a *C. difficile* TcdB toxin mutant as defined elsewhere herein.

The present invention further contemplates an antibody against a *Clostridium difficile* TcdB toxin wherein said antibody is raised against a *C. difficile* TcdB toxin mutant as defined elsewhere herein.

The present invention further contemplates a method of treating a human or animal having, or disposed to having, a *Clostridium difficile* infection, comprising administering to the subject a therapeutically effective amount of an antibody against to an TcdB toxin of *C. difficile*, the antibody raised against a *C. difficile* TcdB toxin mutant as defined elsewhere herein. The method for a *Clostridium difficile* infection may comprise administering a serum comprising the antibodies effective against *C. difficile* TcdB toxin.

The present invention further contemplates a method of making a hybridoma which secretes an antibody against *C. difficile* TcdB toxin, the method comprising fusing a lymphocyte from an animal immunized with a *C. difficile* TcdB toxin mutant with cells capable of replicating indefinitely in cell culture to produce the hybridoma and further isolating the hybridoma. The hybridoma may further secrete an antibody against *C. difficile* TcdB toxin.

Additionally, the present invention further contemplates an immunoassay for *C. difficile* TcdB toxin in which a sample is contacting a sample which may contain a *C. difficile* TcdB toxin or a portion thereof with an antibody raised against a *C. difficile* TcdB toxin mutant to form an antibody-TcdB toxin complex and further detecting the antibody-TcdB toxin complex to determine the presence of the *C. difficile* TcdB toxin.

The present invention further contemplates a polynucleotide which encodes a mutant of *C. difficile* TcdB toxin polypeptide as defined herein. In addition, the present invention further contemplates a vector containing a polynucleotide which encodes a mutant of *C. difficile* TcdB toxin polypeptide as defined herein. The present invention further contemplates a host cell containing a vector containing a polynucleotide which encodes a mutant of *C. difficile* TcdB toxin polypeptide as defined herein. The present invention further contemplates a process for producing a mutant of *C. difficile* TcdB toxin polypeptide by culturing the host cell described herein thereby expressing the mutant and purifying the mutant from the cultured host cell. The present invention further contemplates a non-toxic mutant of *C. difficile* TcdB toxin comprising a substitution in the cysteine residue of the native form of the toxin.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings.

What is claimed is:

1. An isolated mutant of *Clostridium difficile* TcdB toxin polypeptide which comprises:
a modified *C. difficile* TcdB toxin polypeptide (SEQ ID NO: 11) wherein the cysteine residue at position 395 of the native *C. difficile* TcdB toxin has been replaced with another amino acid, wherein the mutant is effective in inhibiting or modulating the cytotoxic effect of *C. difficile* TcdB toxin and *C. sordellii* TcsL toxin.

2. The mutant of claim 1 wherein the substituted amino acid at position 395 is tryptophan.

3. The mutant of claim 1 wherein the substituted amino acid in at position 395 is selected from the group consisting of alanine, aspartic acid, glutamic acid, phenylalanine, glycine, histidine, isoleucine, lysine, leucine, methionine, asparagine, proline, glutamine, arginine, serine, threonine, valine, and tyrosine.

* * * * *

UNITED STATES PATENT AND TRADEMARK OFFICE
CERTIFICATE OF CORRECTION

| | | |
|---|---|---|
| PATENT NO. | : 7,226,597 B2 | Page 1 of 1 |
| APPLICATION NO. | : 10/463957 | |
| DATED | : June 5, 2007 | |
| INVENTOR(S) | : Jimmy D. Ballard and Lea M. Spyres | |

It is certified that error appears in the above-identified patent and that said Letters Patent is hereby corrected as shown below:

In the Specification:
Column 13, line 9: Delete "XLI-blue" and replace with -- XL1-blue --.

Column 14, line 21: Delete "(GNNATGG)" and replace with -- (GNN<u>AT</u>GG) --.

Column 14, lines 23 & 25: Delete "(INITROGEN)" and replace with
-- (INVITROGEN) --.

Signed and Sealed this

Seventh Day of August, 2007

JON W. DUDAS
*Director of the United States Patent and Trademark Office*

SEQUENCE LISTING

<160> NUMBER OF SEQ ID NOS: 18

<210> SEQ ID NO 1
<211> LENGTH: 556
<212> TYPE: PRT
<213> ORGANISM: Clostridium difficile

<400> SEQUENCE: 1

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285
```

```
Met Leu Pro Gly Ile Gln Pro Asp Leu Phe Glu Ser Ile Glu Lys Pro
        290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
            325                 330                 335
Met Leu Asp Glu Glu Val Gln Ser Ser Phe Glu Ser Val Leu Ala Ser
        340                 345                 350
Lys Ser Asp Lys Ser Glu Ile Phe Ser Ser Leu Gly Asp Met Glu Ala
    355                 360                 365
Ser Pro Leu Glu Val Lys Ile Ala Phe Asn Ser Lys Gly Ile Ile Asn
370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
            405                 410                 415
Ala Ile Ser Glu Asp Asn Asp Phe Asn Thr Thr Thr Asn Thr Phe Ile
        420                 425                 430
Asp Ser Ile Met Ala Glu Ala Asn Ala Asp Asn Gly Arg Phe Met Met
    435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
            485                 490                 495
Asp Leu Arg Asn Phe Glu Ile Ser Lys Thr Asn Ile Ser Gln Ser Thr
        500                 505                 510
Glu Gln Glu Met Ala Ser Leu Trp Ser Phe Asp Asp Ala Arg Ala Lys
    515                 520                 525
Ala Gln Phe Glu Glu Tyr Lys Arg Asn Tyr Phe Glu Gly Ser Leu Gly
530                 535                 540
Glu Asp Asp Asn Leu Asp Phe Ser Gln Asn Ile Val
545                 550                 555

<210> SEQ ID NO 2
<211> LENGTH: 1668
<212> TYPE: DNA
<213> ORGANISM: Clostridium difficile

<400> SEQUENCE: 2
atgagtttag ttaatagaaa acagttagaa aaaatggcaa atgtaagatt tcgtactcaa      60
gaagatgaat atgttgcaat attggatgct ttagaagaat atcataatat gtcagagaat     120
actgtagtcg aaaatatttt aaaattaaaa gatataaata gtttaacaga tatttatata     180
gatacatata aaaatctgg tagaaataaa gccttaaaaa aatttaagga atatctagtt     240
acagaagtat tagagctaaa gaataataat ttaactccag ttgagaaaaa tttacatttt     300
gtttggattg gaggtcaaat aaatgacact gctattaatt atataaatca atggaaagat     360
gtaaatagtg attataatgt taatgttttt tatgatagta atgcattttt gataaacaca     420
ttgaaaaaaa ctgtagtaga atcagcaata aatgatacac ttgaatcatt tagagaaaac     480
ttaaatgacc ctagatttga ctataataaa ttccttcagaa aacgtatgga aataattttat     540 gataaacaga aaaatttcat aaactactat aaagctcaaa gagaagaaaa tcctgaactt     600
```

-continued

```
ataattgatg atattgtaaa gacatatctt tcaaatgagt attcaaagga gatagatgaa    660
cttaatacct atattgaaga atccttaaat aaaattacac agaatagtgg aaatgatgtt    720
agaaactttg aagaatttaa aaatggagag tcattcaact tatatgaaca agagttggta    780
gaaaggtgga atttagctgc tgcttctgac atattaagaa tatctgcatt aaaagaaatt    840
ggtggtatgt atttagatgt tgatatgtta ccaggaatac aaccagactt atttgagtct    900
atagagaaac ctagttcagt aacagtggat ttttgggaaa tgacaaagtt agaagctata    960
atgaaataca agaatatat accagaatat acctcagaac attttgacat gttagacgaa   1020
gaagttcaaa gtagttttga atctgttcta gcttctaagt cagataaatc agaaatattc   1080
tcatcacttg gtgatatgga ggcatcacca ctagaagtta aaattgcatt taatagtaag   1140
ggtattataa atcaagggct aatttctgtg aaagactcat attgtagcaa tttaatagta   1200
aaacaaatcg agaatagata taaaatattg aataatagtt taaatccagc tattagcgag   1260
gataatgatt ttaatactac aacgaatacc tttattgata gtataatggc tgaagctaat   1320
gcagataatg gtagatttat gatgaaacta ggaaagtatt taagagttgg tttcttccca   1380
gatgttaaaa ctactattaa cttaagtggc cctgaagcat atgcggcagc ttatcaagat   1440
ttattaatgt ttaaagaagg cagtatgaat atccatttga tagaagctga tttaagaaac   1500
tttgaaatct ctaaaactaa tatttctcaa tcaactgaac aagaaatggc tagcttatgg   1560
tcatttgacg atgcaagagc taaagctcaa tttgaagaat ataaaaggaa ttattttgaa   1620
ggttctcttg gtgaagatga taatcttgat ttttctcaaa atatagta                1668
```

<210> SEQ ID NO 3
<211> LENGTH: 500
<212> TYPE: PRT
<213> ORGANISM: Clostridium difficile

<400> SEQUENCE: 3

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
```

```
                180             185             190
Gln Arg Glu Glu Asn Pro Glu Leu Ile Ile Asp Asp Ile Val Lys Thr
        195                 200                 205
Tyr Leu Ser Asn Glu Tyr Ser Lys Glu Ile Asp Glu Leu Asn Thr Tyr
    210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ser Asp Ile Leu
            260                 265                 270
Arg Ile Ser Ala Leu Lys Glu Ile Gly Gly Met Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
            420                 425                 430
Asp Ser Ile Met Ala Glu Ala Asn Ala Asp Asn Gly Arg Phe Met Met
        435                 440                 445
Glu Leu Gly Lys Tyr Leu Arg Val Gly Phe Phe Pro Asp Val Lys Thr
    450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn
        500

<210> SEQ ID NO 4
<211> LENGTH: 1500
<212> TYPE: DNA
<213> ORGANISM: Clostridium difficile

<400> SEQUENCE: 4
atgagtttag ttaatagaaa acagttagaa aaaatggcaa atgtaagatt tcgtactcaa      60
gaagatgaat atgttgcaat attggatgct ttagaagaat atcataatat gtcagagaat     120
actgtagtcg aaaaatattt aaaattaaaa gatataaata gtttaacaga tatttatata     180
gatacatata aaaatctgg tagaaataaa gccttaaaaa aatttaagga atatctagtt     240
acagaagtat tagagctaaa gaataataat ttaactccag ttgagaaaaa tttacatttt     300
```

-continued

```
gtttggattg gaggtcaaat aaatgacact gctattaatt atataaatca atggaaagat    360
gtaaatagtg attataatgt taatgttttt tatgatagta atgcattttt gataaacaca    420
ttgaaaaaaa ctgtagtaga atcagcaata aatgatacac ttgaatcatt tagagaaaac    480
ttaaatgacc ctagatttga ctataataaa ttcttcagaa aacgtatgga ataaatttat    540
gataaacaga aaaatttcat aaactactat aaagctcaaa gagaagaaaa tcctgaactt    600
ataattgatg atattgtaaa gacatatctt tcaaatgagt attcaaagga gatagatgaa    660
cttaataccta tattgaaga atccttaaat aaaattacac agaatagtgg aaatgatgtt    720
agaaactttg aagaatttaa aaatggagag tcattcaact tatatgaaca agagttggta    780
gaaaggtgga atttagctgc tgcttctgac atattaagaa tatctgcatt aaaagaaatt    840
ggtggtatgt atttagatgt tgatatgtta ccaggaatac aaccagactt atttgagtct    900
atagagaaac ctagttcagt aacagtggat ttttgggaaa tgacaaagtt agaagctata    960
atgaaataca agaatatat accagaatat acctcagaac attttgacat gttagacgaa   1020
gaagttcaaa gtagttttga atctgttcta gcttctaagt cagataaatc agaaatattc   1080
tcatcacttg gtgatatgga ggcatcacca ctagaagtta aaattgcatt taatagtaag   1140
ggtattataa atcaagggct aatttctgtg aaagactcat attgtagcaa tttaatagta   1200
aaacaaatcg agaatagata taaatattg aataatagtt taaatccagc tattagcgag   1260
gataatgatt ttaatactac aacgaatacc tttattgata gtataatggc tgaagctaat   1320
gcagataatg gtagatttat gatggaacta ggaaagtatt taagagttgg tttcttccca   1380
gatgttaaaa ctactattaa cttaagtggc cctgaagcat atgcggcagc ttatcaagat   1440
ttattaatgt ttaaagaagg cagtatgaat atccatttga tagaagctga tttaagaaac   1500
```

<210> SEQ ID NO 5
<211> LENGTH: 420
<212> TYPE: PRT
<213> ORGANISM: Clostridium difficile

<400> SEQUENCE: 5

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160
```

-continued

```
Leu Asn Asp Pro Arg Phe Asp Tyr Asn Lys Phe Phe Arg Lys Arg Met
                165                 170                 175
Glu Ile Ile Tyr Asp Lys Gln Lys Asn Phe Ile Asn Tyr Tyr Lys Ala
            180                 185                 190
Gln Arg Glu Glu Asn Pro Glu Leu Ile Ile Asp Asp Ile Val Lys Thr
        195                 200                 205
Tyr Leu Ser Asn Glu Tyr Ser Lys Glu Ile Asp Glu Leu Asn Thr Tyr
    210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Ile Gly Gly Met Tyr Leu Asp Val Asp
        275                 280                 285
Met Leu Pro Gly Ile Gln Pro Asp Leu Phe Glu Ser Ile Glu Lys Pro
    290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
        355                 360                 365
Ser Pro Leu Glu Val Lys Ile Ala Phe Asn Ser Lys Gly Ile Ile Asn
    370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu
            420
```

```
<210> SEQ ID NO 6
<211> LENGTH: 1260
<212> TYPE: DNA
<213> ORGANISM: Clostridium difficile

<400> SEQUENCE: 6
atgagtttag ttaatagaaa acagttagaa aaaatggcaa atgtaagatt tcgtactcaa      60
gaagatgaat atgttgcaat attggatgct ttagaagaat atcataatat gtcagagaat     120
actgtagtcg aaaatatttt aaaattaaaa gatataaata gtttaacaga tatttatata     180
gatacatata aaaaatctgg tagaaataaa gccttaaaaa aatttaagga atatctagtt     240
acagaagtat tagagctaaa gaataataat ttaactccag ttgagaaaaa tttacatttt     300
gtttggattg gaggtcaaat aaatgacact gctattaatt atataaatca atggaaagat     360
gtaaatagtg attataatgt taatgttttt tatgatagta atgcattttt gataaacaca     420
ttgaaaaaaa ctgtagtaga atcagcaata aatgatacac ttgaatcatt tagagaaaac     480
ttaaatgacc ctagatttga ctataataaa ttcttcagaa aacgtatgga aataattat      540
gataaacaga aaaatttcat aaactactat aaagctcaaa gagaagaaaa tcctgaactt     600
```

-continued

```
ataattgatg atattgtaaa gacatatctt tcaaatgagt attcaaagga gatagatgaa    660
cttaatacct atattgaaga atccttaaat aaaattacac agaatagtgg aaatgatgtt    720
agaaactttg aagaatttaa aaatggagag tcattcaact tatatgaaca agagttggta    780
gaaaggtgga atttagctgc tgcttctgac atattaagaa tatctgcatt aaaagaaatt    840
ggtggtatgt atttagatgt tgatatgtta ccaggaatac aaccagactt atttgagtct    900
atagagaaac ctagttcagt aacagtggat ttttgggaaa tgacaaagtt agaagctata    960
atgaaataca agaatatat accagaatat acctcagaac attttgacat gttagacgaa   1020
gaagttcaaa gtagttttga atctgttcta gcttctaagt cagataaatc agaaatattc   1080
tcatcacttg gtgatatgga ggcatcacca ctagaagtta aaattgcatt taatagtaag   1140
ggtattataa atcaagggct aatttctgtg aaagactcat attgtagcaa tttaatagta   1200
aaacaaatcg agaatagata taaatattg aataatagtt taaatccagc tattagcgag   1260
```

<210> SEQ ID NO 7
<211> LENGTH: 170
<212> TYPE: PRT
<213> ORGANISM: Clostridium difficile

<400> SEQUENCE: 7

```
Met Ser Leu Val Asn Arg Lys Gln Leu Glu Lys Met Ala Asn Val Arg
 1               5                  10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
 65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
           100                 105                 110

Asn Tyr Ile Asn Gln Trp Lys Asp Val Asn Ser Asp Tyr Asn Val Asn
       115                 120                 125

Val Phe Tyr Asp Ser Asn Ala Phe Leu Ile Asn Thr Leu Lys Lys Thr
   130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys
               165                 170
```

<210> SEQ ID NO 8
<211> LENGTH: 510
<212> TYPE: DNA
<213> ORGANISM: Clostridium difficile

<400> SEQUENCE: 8

```
atgagtttag ttaatagaaa acagttagaa aaaatggcaa atgtaagatt tcgtactcaa     60
gaagatgaat atgttgcaat attggatgct ttagaagaat atcataatat gtcagagaat    120
actgtagtcg aaaatatttt aaaattaaaa gatataaata gtttaacaga tatttatata    180
gatacatata aaaatctgg tagaaataaa gccttaaaaa aatttaagga atatctagtt    240
```

```
acagaagtat tagagctaaa gaataataat ttaactccag ttgagaaaaa tttacattttt    300 gtttggattg gaggtcaaat aaatgacact gctattaatt atataaatca atggaaagat    360
gtaaatagtg attataatgt taatgttttt tatgatagta atgcattttt gataaacaca    420
ttgaaaaaaa ctgtagtaga atcagcaata aatgatacac ttgaatcatt tagagaaaac    480
ttaaatgacc ctagatttga ctataataaa                                      510
```

<210> SEQ ID NO 9
<211> LENGTH: 522
<212> TYPE: PRT
<213> ORGANISM: Clostridium difficile

<400> SEQUENCE: 9

```
His Asn Met Ser Glu Asn Thr Val Val Glu Lys Tyr Leu Lys Leu Lys
 1               5                   10                  15

Asp Ile Asn Ser Leu Thr Asp Thr Tyr Ile Asp Thr Tyr Lys Lys Ser
            20                  25                  30

Gly Arg Asn Lys Ala Leu Lys Lys Phe Lys Glu Tyr Leu Val Ile Glu
        35                  40                  45

Ile Leu Glu Leu Glu Asn Ser Asn Leu Thr Pro Val Glu Lys Asn Leu
    50                  55                  60

His Phe Ile Trp Ile Gly Gly Gln Ile Asn Asp Thr Ala Ile Asn Tyr
65                  70                  75                  80

Ile Asn Gln Trp Lys Asp Val Asn Ser Asp Tyr Asn Val Asn Val Phe
                85                  90                  95

Tyr Asp Ser Asn Ala Phe Leu Ile Asn Thr Leu Lys Lys Thr Ile Ile
            100                 105                 110

Glu Ser Ala Ser Asn Asp Thr Leu Glu Ser Phe Arg Glu Asn Leu Asn
        115                 120                 125

Asp Pro Glu Phe Asn His Thr Ala Phe Phe Arg Lys Arg Met Gln Ile
    130                 135                 140

Ile Tyr Asp Lys Gln Gln Asn Phe Ile Asn Tyr Tyr Lys Ala Gln Lys
145                 150                 155                 160

Glu Glu Asn Pro Asp Leu Ile Ile Asp Asp Ile Val Lys Thr Tyr Leu
                165                 170                 175

Ser Asn Glu Tyr Ser Lys Asp Ile Asp Glu Leu Asn Ala Tyr Ile Glu
            180                 185                 190

Glu Ser Leu Asn Lys Val Thr Glu Asn Ser Gly Asn Asp Val Arg Asn
        195                 200                 205

Phe Glu Glu Phe Lys Thr Gly Glu Val Phe Asn Leu Tyr Glu Gln Glu
    210                 215                 220

Leu Val Glu Arg Trp Asn Leu Ala Gly Ala Ser Asp Ile Leu Arg Val
225                 230                 235                 240

Ala Ile Leu Lys Asn Ile Gly Gly Val Tyr Leu Asp Val Asp Met Leu
                245                 250                 255

Pro Gly Ile His Pro Asp Leu Phe Lys Asp Ile Asn Lys Pro Asp Ser
            260                 265                 270

Val Lys Thr Ala Val Asp Trp Glu Glu Met Gln Leu Glu Ala Ile Met
        275                 280                 285

Lys His Lys Glu Tyr Ile Pro Glu Tyr Thr Ser Lys His Phe Asp Thr
    290                 295                 300

Leu Asp Glu Glu Val Gln Ser Ser Phe Glu Ser Val Leu Ala Ser Lys
305                 310                 315                 320

Ser Asp Lys Ser Glu Ile Phe Leu Pro Leu Gly Asp Ile Glu Val Ser
```

```
                    325                 330                 335
Pro Leu Glu Val Lys Ile Ala Phe Ala Lys Gly Ser Ile Ile Asn Gln
            340                 345                 350

Ala Leu Ile Ser Ala Lys Asp Ser Tyr Cys Ser Asp Leu Leu Ile Lys
        355                 360                 365

Gln Ile Gln Asn Arg Tyr Lys Ile Leu Asn Asp Thr Leu Gly Pro Ile
    370                 375                 380

Ile Ser Gln Gly Asn Asp Phe Asn Thr Thr Met Asn Asn Phe Gly Glu
385                 390                 395                 400

Ser Leu Gly Ala Ile Ala Asn Glu Glu Asn Ile Ser Phe Ile Ala Lys
                405                 410                 415

Ile Gly Ser Tyr Leu Arg Val Gly Phe Tyr Pro Glu Ala Asn Thr Thr
            420                 425                 430

Val Thr Leu Ser Gly Pro Thr Ile Tyr Ala Gly Ala Tyr Lys Asp Leu
        435                 440                 445

Leu Thr Phe Lys Glu Met Ser Ile Asp Thr Ser Ile Leu Ser Ser Glu
    450                 455                 460

Leu Arg Asn Phe Glu Phe Pro Lys Val Asn Ile Ser Gln Ala Thr Glu
465                 470                 475                 480

Gln Glu Lys Asn Ser Leu Trp Gln Phe Asn Glu Glu Arg Ala Lys Ile
                485                 490                 495

Gln Phe Glu Glu Tyr Lys Lys Asn Tyr Phe Glu Gly Ala Leu Gly Glu
            500                 505                 510

Asp Asp Asn Leu Asp Phe Ser Gln Asn Thr
        515                 520

<210> SEQ ID NO 10
<211> LENGTH: 1566
<212> TYPE: DNA
<213> ORGANISM: Clostridium difficile

<400> SEQUENCE: 10
cataatatgt cagagaatac tgtagtcgaa aaatatttaa aattaaaaga tataaatagt      60
ttaacagata tttatataga tacatataaa aaatctggta gaaataaagc cttaaaaaaa     120
tttaaggaat atctagttac agaagtatta gagctaaaga ataataattt aactccagtt     180
gagaaaaatt tacattttgt ttggattgga ggtcaaataa atgacactgc tattaattat     240
ataaatcaat ggaaagatgt aaatagtgat tataatgtta atgtttttta tgatagtaat     300 gcattttga taaacacatt gaaaaaaact gtagtagaat cagcaataaa tgatacactt     360
gaatcattta gagaaaactt aaatgaccct agatttgact ataataaatt cttcagaaaa     420
cgtatggaaa taatttatga taaacagaaa aatttcataa actactataa agctcaaaga     480
gaagaaaatc ctgaacttat aattgatgat attgtaaaga catatctttc aaatgagtat     540
tcaaaggaga tagatgaact taatacctat attgaagaat ccttaaataa aattacacag     600
aatagtggaa atgatgttag aaactttgaa gaatttaaaa atggagagtc attcaactta     660
tatgaacaag agttggtaga aggtggaatt tagctgctg cttctgacat attaagaata     720
tctgcattaa agaaattgg tggtatgtat ttagatgttg atatgttacc aggaatacaa     780
ccagacttat ttgagtctat agagaaacct agttcagtaa cagtggattt ttgggaaatg     840
acaaagttag aagctataat gaaatacaaa gaatatatac cagaatatac ctcagaacat     900
tttgacatgt tagacgaaga agttcaaagt agttttgaat ctgttctagc ttctaagtca     960
gataaatcag aaatattctc atcacttggt gatatggagg catcaccact agaagttaaa    1020
```

```
attgcattta atagtaaggg tattataaat caagggctaa tttctgtgaa agactcatat   1080
tgtagcaatt taatagtaaa acaaatcgag aatagatata aaatattgaa taatagttta   1140
aatccagcta ttagcgagga taatgatttt aatactacaa cgaatacctt tattgatagt   1200
ataatggctg aagctaatgc agataatggt agatttatga tggaactagg aaagtattta   1260
agagttggtt tcttcccaga tgttaaaact actattaact taagtggccc tgaagcatat   1320
gcggcagctt atcaagattt attaatgttt aaagaaggca gtatgaatat ccatttgata   1380
gaagctgatt taagaaactt tgaaatctct aaaactaata tttctcaatc aactgaacaa   1440
gaaatggcta gcttatggtc atttgacgat gcaagagcta aagctcaatt tgaagaatat   1500
aaaaggaatt attttgaagg ttctcttggt gaagatgata atcttgattt ttctcaaaat   1560
atagta                                                             1566
```

<210> SEQ ID NO 11
<211> LENGTH: 556
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (395)..(395)
<223> OTHER INFORMATION: Xaa at position 395 is ala, asp, glu, phe, gly,
      his, ile, lys, leu, met, asn, pro, gln, arg, ser, thr, val, trp,
      or tyr.

<400> SEQUENCE: 11

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220
```

```
Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
            245                 250                 255

Gln Glu Leu Val Glu Arg Trp Asn Leu Ala Ala Ala Ser Asp Ile Leu
        260                 265                 270

Arg Ile Ser Ala Leu Lys Glu Ile Gly Gly Met Tyr Leu Asp Val Asp
    275                 280                 285

Met Leu Pro Gly Ile Gln Pro Asp Leu Phe Glu Ser Ile Glu Lys Pro
290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
            325                 330                 335

Met Leu Asp Glu Glu Val Gln Ser Ser Phe Glu Ser Val Leu Ala Ser
        340                 345                 350

Lys Ser Asp Lys Ser Glu Ile Phe Ser Ser Leu Gly Asp Met Glu Ala
    355                 360                 365

Ser Pro Leu Glu Val Lys Ile Ala Phe Asn Ser Lys Gly Ile Ile Asn
370                 375                 380

Gln Gly Leu Ile Ser Val Lys Asp Ser Tyr Xaa Ser Asn Leu Ile Val
385                 390                 395                 400

Lys Gln Ile Glu Asn Arg Tyr Lys Ile Leu Asn Asn Ser Leu Asn Pro
            405                 410                 415

Ala Ile Ser Glu Asp Asn Asp Phe Asn Thr Thr Asn Thr Phe Ile
        420                 425                 430

Asp Ser Ile Met Ala Glu Ala Asn Ala Asp Asn Gly Arg Phe Met Met
    435                 440                 445

Glu Leu Gly Lys Tyr Leu Arg Val Gly Phe Phe Pro Asp Val Lys Thr
450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
            485                 490                 495

Asp Leu Arg Asn Phe Glu Ile Ser Lys Thr Asn Ile Ser Gln Ser Thr
        500                 505                 510

Glu Gln Glu Met Ala Ser Leu Trp Ser Phe Asp Asp Ala Arg Ala Lys
    515                 520                 525

Ala Gln Phe Glu Glu Tyr Lys Arg Asn Tyr Phe Glu Gly Ser Leu Gly
530                 535                 540

Glu Asp Asp Asn Leu Asp Phe Ser Gln Asn Ile Val
545                 550                 555

<210> SEQ ID NO 12
<211> LENGTH: 556
<212> TYPE: PRT
<213> ORGANISM: Clostridium difficile

<400> SEQUENCE: 12

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45
```

```
-continued

Leu Lys Asp Ile Asn Ser Leu Thr Asp Ile Tyr Ile Asp Thr Tyr Lys
     50                  55                  60

Lys Ser Gly Arg Asn Lys Ala Leu Lys Lys Phe Lys Glu Tyr Leu Val
 65              70                  75                      80

Thr Glu Val Leu Glu Leu Lys Asn Asn Asn Leu Thr Pro Val Glu Lys
                     85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460
```

```
Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
            485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val
545                 550                 555

<210> SEQ ID NO 13
<211> LENGTH: 38
<212> TYPE: DNA
<213> ORGANISM: Artificial sequence
<220> FEATURE:
<223> OTHER INFORMATION: Completely synthesized

<400> SEQUENCE: 13
gtttactatt aaattgctag aatatgagtc tttcacag                    38

<210> SEQ ID NO 14
<211> LENGTH: 38
<212> TYPE: DNA
<213> ORGANISM: Artificial sequence
<220> FEATURE:
<223> OTHER INFORMATION: Completely synthesized

<400> SEQUENCE: 14
ctgtgaagac tcatattcta gcaatttaat agtaaaac                    38

<210> SEQ ID NO 15
<211> LENGTH: 38
<212> TYPE: DNA
<213> ORGANISM: Artificial sequence
<220> FEATURE:
<223> OTHER INFORMATION: Completely synthesized

<400> SEQUENCE: 15
gttttactat taaattgcta cctatgagtc tttcacag                    38

<210> SEQ ID NO 16
<211> LENGTH: 39
<212> TYPE: DNA
<213> ORGANISM: Artificial sequence
<220> FEATURE:
<223> OTHER INFORMATION: Completely synthesized

<400> SEQUENCE: 16
ctgtgaaaga ctcatattgg agcaatttaa tagtaaaac                   39

<210> SEQ ID NO 17
<211> LENGTH: 33
<212> TYPE: DNA
<213> ORGANISM: Artificial sequence
<220> FEATURE:
<223> OTHER INFORMATION: Completely synthesized

<400> SEQUENCE: 17
aaaaatttac attttgttgc tattggaggt caa                         33
```

```
<210> SEQ ID NO 18
<211> LENGTH: 33
<212> TYPE: DNA
<213> ORGANISM: Artificial sequence
<220> FEATURE:
<223> OTHER INFORMATION: Completely synthesized

<400> SEQUENCE: 18
ttgacctcca atagcaacaa aatgtaaatt ttt                                    33
```